US012760035B2

(12) United States Patent
Gray et al.

(10) Patent No.: US 12,760,035 B2
(45) Date of Patent: Oct. 13, 2026

(54) COVALENT EGFR INHIBITORS AND METHODS OF USE THEREOF

(71) Applicant: Dana-Farber Cancer Institute, Inc., Boston, MA (US)

(72) Inventors: Nathanael S. Gray, Boston, MA (US); Zhengnian Li, Boston, MA (US); Jianwei Che, Sharon, MA (US); Tinghu Zhang, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 398 days.

(21) Appl. No.: 18/549,127

(22) PCT Filed: Mar. 2, 2022

(86) PCT No.: PCT/US2022/018524
§ 371 (c)(1),
(2) Date: Sep. 5, 2023

(87) PCT Pub. No.: WO2022/187363
PCT Pub. Date: Sep. 9, 2022

(65) Prior Publication Data

US 2024/0166665 A1 May 23, 2024

Related U.S. Application Data

(60) Provisional application No. 63/155,623, filed on Mar. 2, 2021.

(51) Int. Cl.

| | |
|---|---|
| ***C07D 498/18*** | (2006.01) |
| ***A61K 31/4152*** | (2006.01) |
| ***A61K 31/439*** | (2006.01) |
| ***A61K 31/496*** | (2006.01) |
| ***A61K 31/504*** | (2006.01) |
| ***A61P 35/00*** | (2006.01) |
| ***C07D 515/22*** | (2006.01) |

(52) U.S. Cl.
CPC ........ *C07D 498/18* (2013.01); *A61K 31/4152* (2013.01); *A61K 31/439* (2013.01); *A61K 31/496* (2013.01); *A61K 31/504* (2013.01); *A61P 35/00* (2018.01); *C07D 515/22* (2013.01)

(58) Field of Classification Search
None
See application file for complete search history.

(56) References Cited

U.S. PATENT DOCUMENTS

2018/0117059 A1 5/2018 Le et al.
2019/0040065 A1 2/2019 Gray et al.
2022/0380382 A1* 12/2022 Engelhardt ............. A61P 35/00

FOREIGN PATENT DOCUMENTS

WO WO 2014/081718 A1 5/2014
WO WO 2019/164949 A1 8/2019
WO WO-2020260252 A1 * 12/2020 ........... C07D 498/22

OTHER PUBLICATIONS

International Search Report and Written Opinion for International Application No. PCT/US2022/018524 mailed Jun. 3, 2022, 7 pages.
Li Z. et al., Molecular Bidents with Two Electrophilic Warheads as a New Pharmacological Modality, ACS Central Science, 2024, pp. 1156-1166, vol. 10, No. 6.
Communication extended European search report, EP Application No. 22763978.8, dated Apr. 25, 2025, 7 pages.

* cited by examiner

*Primary Examiner* — Jeffrey S Lundgren
*Assistant Examiner* — Anthony Joseph Seitz
(74) *Attorney, Agent, or Firm* — Nielsen IP Law LLC

(57) ABSTRACT

The disclosure relates to compounds that act as covalent inhibitors of epidermal growth factor receptor (EGFR); pharmaceutical compositions comprising the compounds; and methods of treating or preventing kinase-mediated disorders, including cancer and other proliferation diseases.

19 Claims, No Drawings

COVALENT EGFR INHIBITORS AND METHODS OF USE THEREOF

RELATED APPLICATIONS

This application claims priority to U.S. Provisional Application No. 63/155,623 filed on Mar. 2, 2021, the entire content of which is hereby incorporated in its entirety.

BACKGROUND

The epidermal growth factor receptor (EGFR, Erb-B1) belongs to a family of receptor tyrosine kinases that mediate the proliferation, differentiation, and survival of normal and malignant cells (Arteaga, C. L., *J. Clin. Oncol.* 19, 2001, 32-40). Deregulation of EGFR has been implicated in many types of human cancer, with overexpression of the receptor present in at least 70% of human cancers (Seymour, L. K., *Curr. Drug Targets* 2, 2001, 117-133), including non-small lung cell carcinomas, breast cancers, gliomas, squamous cell carcinomas of the head and neck, and prostate cancer (Raymond, E., et al., *Drugs* 60 (Suppl. 1), 2000, 15-23, discussion 41-2; Salomon, D. S., et al., *Crit. Rev. Oncol. Hematol.* 19, 1995, 183-232; Voldborg B. R., et al., *Ann. Oncol.* 8, 1997, 1197-1206). EGFR has, therefore, emerged as an attractive target for the design and development of diagnostic and therapeutic agents that can specifically bind and inhibit the receptor's tyrosine kinase activity and signal transduction pathway in cancer cells. For example, the EGFR tyrosine kinase (EGFR-TK) reversible inhibitor TARCEVA® is approved by the FDA for treatment of NSCLC and advanced pancreatic cancer. Other anti-EGFR targeted molecules have also been approved, including LAPATINIB and IRESSA®.

Epidermal growth factor receptor (EGFR) tyrosine kinase inhibitors (TKIs) are effective clinical therapies for EGFR mutant advanced non-small cell lung cancer (NSCLC) patients (Mok, T. S., et al., *N. Engl. J. Med.* 361, 2009, 947-57; Paez, J. G., et al., *Science* 304, 2004, 1497-500; Lynch, T. J., et al., *N. Engl. J. Med.* 350, 2004, 2129-39; Rosell, R., et al., *Lancet Oncol.* 13, 2012, 239-46). Several randomized clinical trials have demonstrated that EGFR TKIs are more effective, as measured by response rate (RR) and progression free survival (PFS), than chemotherapy when used as initial systemic treatment for advanced EGFR mutant NSCLC (Mok, T. S., et al., *N. Engl. J. Med.* 361, 2009, 947-57; Rosell, R., et al., *Lancet Oncol.* 13, 2012, 239-46; Sequest, L. V. et al., *J. Clin. Oncol.* 31, 2013, 3327-34; Wu, Y. L., et al., *Lancet Oncol.* 15, 2014, 213-22; Maemondo, M., et al., *N. Engl. J. Med.* 362, 2010, 2380-8; Zhou, C., et al., *Lancet Oncol.* 12, 2011, 735-42; Mitsudomi, T., et al., *Lancet Oncol.* 11, 2010, 121-8). However, the vast majority of patients will develop disease progression following successful treatment with an EGFR TKI. The most common mechanism of acquired resistance, detected in 60% of patients, is a secondary mutation in EGFR at position T790 (T790M) (Yu, H. A., et al., *Clin. Cancer Res.* 19, 2013, 2240-7). This mutation leads to an increase in ATP affinity, thus making it more difficult for reversible EGFR TKIs gefitinib and erlotinib to bind the EGFR TKI domain (Yun C. H., et al., *Proc. Natl. Acad. Sci. USA* 105, 2008, 2070-5).

Covalent EGFR inhibitors have emerged for inhibiting EGFR T790M-containing cancers. However, in lung cancer patients, afatinib is only effective in EGFR TKI naïve EGFR mutant cancers and has a RR of less than 10% in patients with NSCLC that have developed resistance to gefitinib or erlotinib (Miller, V. A., et al., *Lancet Oncol.* 13, 2012, 528-38). Afatinib is a potent inhibitor of both mutant and wild type (WT) EGFR. Inhibition of WT EGFR leads to toxicities, including skin rash and diarrhea, which limits the ability to escalate afatinib doses in patients to those necessary to inhibit EGFR T790M. Irreversible pyrimidine EGFR inhibitors including the tool compound WZ4002 and clinical compounds CO-1686 and AZD9291, overcome many of the limitations of afatinib (Zhou, W., et al., *Nature* 462, 2009, 1070-4; Walter, A. O., et al., *Cancer Discov.* 3, 2013, 1404-15; Cross, D. A. E., et al., *Cancer Discov.* 4, 2014, 1046-61). They are not only more potent on EGFR T790M, but also selectively inhibit mutant over WT EGFR and hence should lead to increased clinical efficacy and less toxicity compared with afatinib (Zhou, W., et al; Walter A. O., et al, Cross, D. A. E., et al.).

However, all current EGFR TKIs target the ATP site, and while third generation irreversible inhibitors can overcome T790M, they are all rendered impotent by the $C_{797}S$ mutation, which is already arising in treated patients. Cetuximab, an anti-EGFR antibody that blocks receptor dimerization, is not effective in EGFR-mutant NSCLC because mutational activation of the kinase is effectively "downstream" of receptor dimerization. Hence, alternative strategies to inhibit EGFR are needed. At present, suitable compounds with alternative mechanisms of action targeting mutant EGFR are not available. Thus, there is a need for potent small molecule EGFR inhibitors with alternative mechanisms of action targeting mutant EGFR.

SUMMARY

In an aspect, provided herein is a compound of Formula I:

(I)

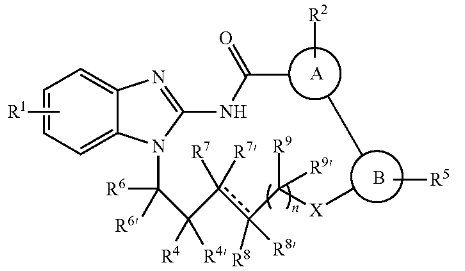

or a pharmaceutically acceptable salt thereof; wherein the variables are defined herein.

In an embodiment, the compound of Formula I is a compound of Formula II:

(II)

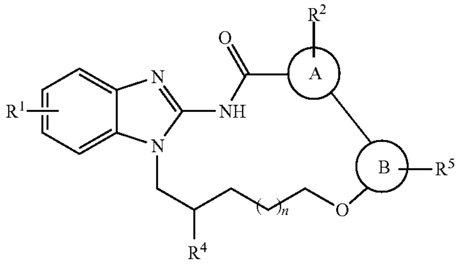

or a pharmaceutically acceptable salt thereof.

In an aspect, provided herein is a method of treating cancer or a proliferation disease, comprising administering to a subject in need thereof an effective amount of a compound disclosed herein or a pharmaceutical composition comprising a compound disclosed herein and a pharmaceutically acceptable carrier. In one embodiment, the cancer is lung cancer, breast cancer, glioma, squamous cell carcinoma, or prostate cancer. In another embodiment, the cancer is non-small cell lung cancer (NSCLC).

In another aspect, provided herein is a method of inhibiting the activity of EGFR, comprising administering to a subject in need thereof an effective amount of a compound of disclosed herein or a pharmaceutical composition comprising a compound disclosed herein and a pharmaceutically acceptable carrier. In an embodiment, the compound targets Cys775 on EGFR.

The disclosure also provides a kit comprising a compound capable of inhibiting EGFR activity selected from a compound of the present disclosure, or a pharmaceutically acceptable salt thereof, and instructions for use in treating cancer. In one embodiment, the kit further comprises components for performing a test to determine whether a subject has an activating mutation in EGFR or a resistance mutation in EGFR

DETAILED DESCRIPTION

Definitions

Listed below are definitions of various terms used to describe the compounds and compositions disclosed herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "administration" or the like as used herein refers to the providing a therapeutic agent to a subject. Multiple techniques of administering a therapeutic agent exist in the art including, but not limited to, intravenous, oral, aerosol, parenteral, ophthalmic, pulmonary, and topical administration.

The term "treat," "treated," "treating," or "treatment" includes the diminishment or alleviation of at least one symptom associated or caused by the state, disorder or disease being treated. In certain embodiments, the treatment comprises bringing into contact with wild-type or mutant EGFR an effective amount of a compound disclosed herein for conditions related to cancer.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the disclosure and a co- agent, are both administered to a patient simultaneously in the form of a single entity or dosage. The term "non-fixed combination" means that the active ingredients, e.g. a compound of the disclosure and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the present disclosure, and are physiologically acceptable to the patient. Supplementary active compounds may also be incorporated into the compositions. The "pharmaceutically acceptable carrier" may further include a pharmaceutically acceptable salt of the compound disclosed herein. Other additional ingredients that may be included in the pharmaceutical compositions are known in the art and described, for example, in Remington's Pharmaceutical Sciences (Genaro, Ed., Mack Publishing Co., 1985, Easton, PA), which is incorporated herein by reference.

As used herein, the term "EGFR" refers to epidermal growth factor receptor (alternately referred to as ErbB-1 or HER1) and may refer to the wild-type receptor or to a receptor containing one or more mutations.

As used herein, the term "HER" or Her" refers to members of the ErbB receptor tyrosine kinase family, including EGFR, ERBB2, HER3, and HER4.

As used herein, the term "allosteric site" refers to a site on EGFR other than the ATP binding site, such as that characterized in a crystal structure of EGFR. An "allosteric site" can be a site that is close to the ATP binding site, such as that characterized in a crystal structure of EGFR. For example, one allosteric site includes one or more of the following amino acid residues of epidermal growth factor receptor (EGFR): Lys745, Leu788, Ala743, Cys775, Leu777, Phe856, Asp855, Met766, lle759, Glu762, and/or Ala763.

As used herein, the term "agent that prevents EGFR dimer formation," or iterations thereof, refers to an agent that prevents dimer formation in which the C-lobe of the "activator" subunit impinges on the N-lobe of the "receiver" subunit. Examples of agents that prevent EGFR dimer formation include, but are not limited to, cetuximab, trastuzumab, panitumumab, and Mig6.

As used herein, the term "alkyl," by itself or as part of another substituent means, unless otherwise stated, a straight or branched chain hydrocarbon having the number of carbon atoms designated (i.e., $C_1$-$C_6$ alkyl means an alkyl having one to six carbon atoms) and includes straight and branched chains. Examples include methyl, ethyl, propyl, isopropyl, butyl, isobutyl, tert butyl, pentyl, neopentyl, and hexyl. Other examples of $C_1$-$C_6$ alkyl include ethyl, methyl, isopropyl, isobutyl, n-pentyl, and n-hexyl.

As used herein, the term "haloalkyl" refers to an alkyl group, as defined above, substituted with one or more halo substituents, wherein alkyl and halo are as defined herein. Haloalkyl includes, by way of example, chloromethyl, trifluoromethyl, bromoethyl, chlorofluoroethyl, and the like.

As used herein, the term "alkoxy" refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "alkenyl" refers to a monovalent group derived from a hydrocarbon moiety containing, in certain embodiments, from two to six, or two to eight carbon atoms having at least one carbon-carbon double bond. The alkenyl group may or may not be the point of attachment to another group. The term "alkenyl" includes, but is not limited to, ethenyl, 1-propenyl, 1-butenyl, heptenyl, octenyl and the like.

As used herein, the term "alkynyl" refers to a monovalent group derived from a hydrocarbon moiety containing, in certain embodiments, from two to six, or two to eight carbon atoms having at least one carbon-carbon triple bond. The alkynyl group may or may not be the point of attachment to another group. The term "alkynyl" includes, but is not limited to, ethynyl, 1-propynyl, 1-butynyl, heptynyl, octynyl and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl.

As used herein, the term "cycloalkenyl" means a non-aromatic carbocyclic system that is partially saturated having 1, 2 or 3 rings wherein such rings may be fused, and wherein at least one ring contains an $sp^2$ carbon-carbon bond. The term "cycloalkenyl" includes, but is not limited to, cyclopropenyl, cyclobutenyl, cyclopentenyl, cyclohexenyl, bicyclo[3.1.0]hexenyl, spiro[3.3]heptanenyl, and bicyclo[1.1.1]pentenyl.

As used herein, the term "heterocyclyl" or "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. The term "heterocyclyl" includes cyclic esters (i.e., lactones) and cyclic amides (i.e., lactams) and also specifically includes, but is not limited to, epoxidyl, oxetanyl, tetrahydro-furanyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]-hexanyl, 6-azabicyclo[3.1.1] heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl.

As used herein, the term "heterocycloalkenyl" means a non-aromatic carbocyclic system containing 1, 2, 3 or 4 heteroatoms selected independently from N, O, and S that is partially saturated having 1, 2 or 3 rings wherein such rings may be fused, and wherein at least one ring contains an $sp^2$ carbon-carbon bond.

As used herein, the term "aromatic" refers to a carbocycle or heterocycle with one or more polyunsaturated rings and having aromatic character, i.e., having (4n+2) delocalized $\pi$ (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta-[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thienyl, and so forth.

As used herein, the phrase "nitrogen protecting group" refers to a functional group bound to a nitrogen atom to obtain chemoselectivity in a subsequent chemical reaction.

Examples of nitrogen protecting groups include, but are not limited to, carbobenzyloxy (Cbz), tent-butyloxycarbonyl (Boc), 9-fluorenylmethyloxycarbonyl (Fmoc), acetyl (Ac), benzoyl (Bz), benzyl (Bn), tosyl (Ts), and p-methoxybenzyl (PMB).

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

Compounds

Provided herein are compounds that are covalent inhibitors of epidermal growth factor receptor (EGFR) useful in the treatment of kinase-mediated disorders, including cancer and other proliferation diseases.

In an aspect, provided herein is a compound of Formula I:

(I)

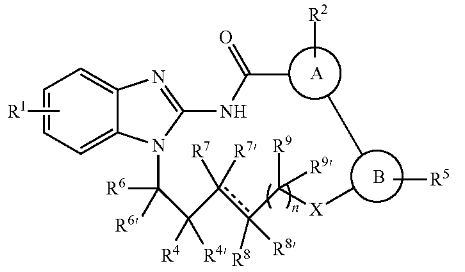

or a pharmaceutically acceptable salt thereof;

wherein:

$\equiv$ is an optional double bond;

X is O, S, or NH;

A is selected from the group consisting of $C_6$-$C_{10}$ aryl, 5-10 membered heteroaryl, $C_3$-$C_{10}$ cycloalkyl, 3-10 membered heterocycloalkyl, $C_3$-$C_{10}$ cycloalkenyl, and 3-10 membered heterocycloalkenyl;

B is selected from the group consisting of $C_6$-$C_{10}$ aryl, 5-10 membered heteroaryl, $C_3$-$C_{10}$ cycloalkyl, 3-10 membered heterocycloalkyl, $C_3$-$C_{10}$ cycloalkenyl, and 3-10 membered heterocycloalkenyl;

$R^1$ is selected from the group consisting of H, halo, OH, $NH_2$, CN, $NO_2$, $C_{1-6}$ alkyl, NH($C_{1-6}$ alkyl), N($C_{1-6}$ alkyl)$_2$, $C_{1-6}$ haloalkyl, $C_{1-6}$ alkoxy, C(O)-$C_1$-$C_6$ alkyl, C(O)$NH_2$, C(O)NH—$C_1$-$C_6$ alkyl, $C_1$-$C_6$ alkyl-OH, P(O)($C_1$-$C_6$ alkyl)$_2$, $C_6$-$C_{10}$ aryl, 5-10 membered heteroaryl, $C_3$-$C_{10}$ cycloalkyl, and 3-10 membered heterocycloalkyl, wherein $C_{1-6}$ alkyl, $C_6$-$C_{10}$ aryl, 5-10 membered heteroaryl, $C_3$-$C_{10}$ cycloalkyl, and 3-10 membered heterocycloalkyl are each optionally substituted with $R^a$;

$R^4$ is selected from the group consisting of H, halo, OH, $NH_2$, $C_{1-6}$ alkyl, $C_{2-6}$ alkenyl, $C_{2-6}$ alkynyl, NH($C_{1-6}$ alkyl), N($C_{1-6}$ alkyl)$_2$, $C_{1-6}$ haloalkyl, $C_{1-6}$ alkoxy, $C_{1-6}$ alkyl-OH, $C_6$-$C_{10}$ aryl, 5-10 membered heteroaryl, $C_3$-$C_{10}$ cycloalkyl, and 3-10 membered heterocycloalkyl;

$R^5$ is selected from the group consisting of H, halo, OH, $NH_2$, $C_{1-6}$ alkyl, $C_{2-6}$ alkenyl, $C_{2-6}$ alkynyl, NH($C_{1-6}$ alkyl), N($C_{1-6}$ alkyl)$_2$, $C_{1-6}$ haloalkyl, $C_{1-6}$ alkoxy, $C_6$-$C_{10}$ aryl, 5-10 membered heteroaryl, $C_3$-$C_{10}$ cycloalkyl, and 3-10 membered heterocycloalkyl;

each $R^{4'}$, $R^6$, $R^{6'}$, $R^7$, $R^{7'}$, $R^8$, $R^{8'}$, $R^9$, and $R^{9'}$ is independently selected from the group consisting of H, halo, OH, $NH_2$, $C_{1-6}$ alkyl, $C_{2-6}$ alkenyl, $C_{2-6}$ alkynyl, NH($C_{1-6}$ alkyl), N($C_{1-6}$ alkyl)$_2$, $C_{1-6}$ haloalkyl, $C_{1-6}$ alkoxy, $C_{1-6}$ alkyl-OH, $C_6$-$C_{10}$ aryl, 5-10 membered heteroaryl, $C_3$-$C_{10}$ cycloalkyl, and 3-10 membered heterocycloalkyl; wherein aryl, heteroaryl, cycloalkyl, and heterocycloalkyl are each optionally substituted with $C_{1-3}$ alkyl;

$R^a$ is selected from the group consisting of $C_6$-$C_{10}$ aryl, 5-10 membered heteroaryl, $C_3$-$C_{10}$ cycloalkyl, and 3-10 membered heterocycloalkyl all of which are optionally substituted with $C_{1-3}$ alkyl;

$R^2$ is selected from the group consisting of:

(i-1)

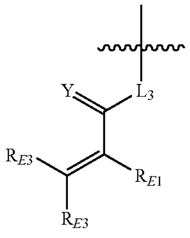

(i-2)

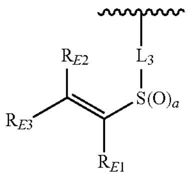

-continued (i-3)

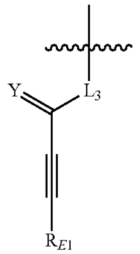

(i-4)

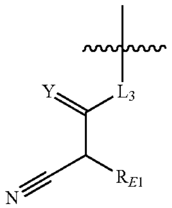

(i-6)

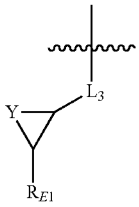

(i-7)

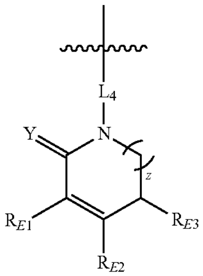

(i-8)

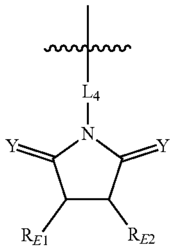

(i-9)

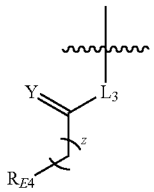

(i-11)

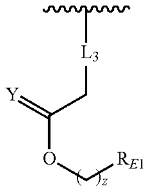

-continued
(i-12)
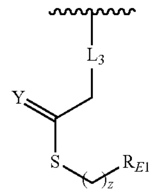
(i-13)
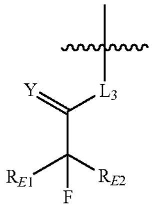
(i-14)
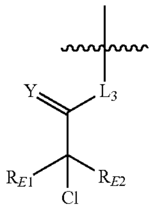
(i-16)
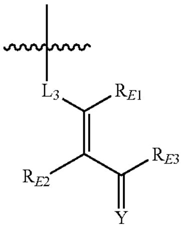
(i-17)
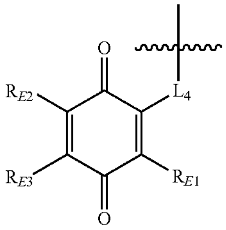
(i-18)
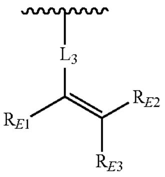
(i-19)
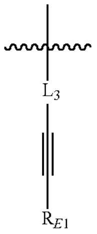
-continued
(i-21)
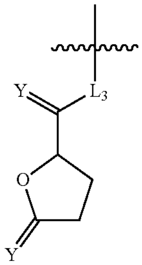
(i-22)
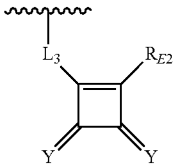
(i-23)
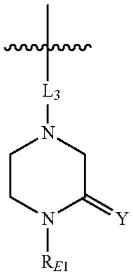
(i-24)
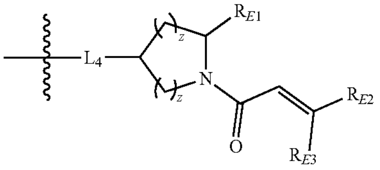
(i-26)
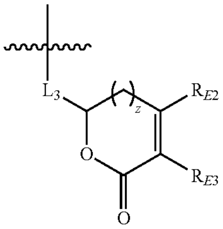
(i-27)
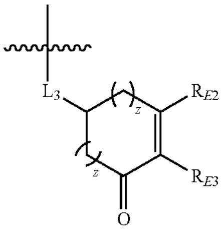
(i-28)
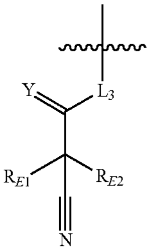

-continued (i-29)

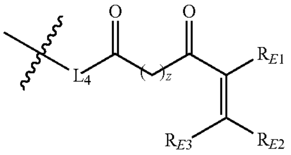

(i-31)

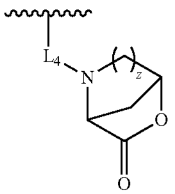

(i-32)

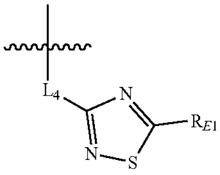

(i-33)

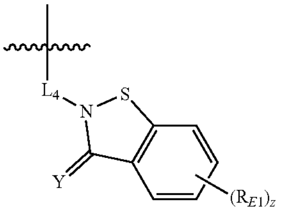

(i-34)

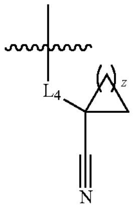

(i-36)

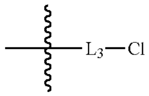

(i-37)

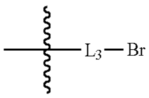

(i-38)

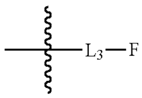

(i-39)

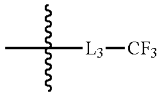

-continued (i-40)

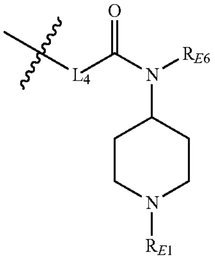

(i-41)

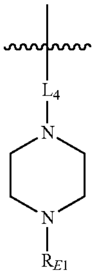

(i-42)

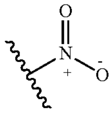

(i-43)

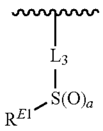

(i-44)

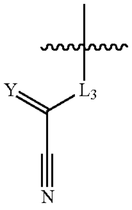

and (i-45)

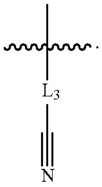

$L_3$ is a bond, —NH—, or $C_1$-$C_4$ alkylene, optionally wherein one or more carbon is independently replaced with —C(O)—, —O—, —S—, —$NR_{L3a}$—, —$NR_{L3a}$C(O)—, —C(O)$NR_{L3a}$—, —C(O)$NR_{L3a}$—, —SC(O)—, —C(O)S—, —OC(O)—, —C(O)O—, —$NR_{L3a}$C(S)—, —C(S)$NR_{L3a}$—, trans-$CR_{L3b}$═$CR_{L3b}$—, cis-$CR_{L3b}$═$CR_{L3b}$—, —C≡C—, S(O)—, —S(O)O—, —OS(O)—, —S(O)$NR_{L3}$—, —$NR_{L3a}$S(O)—, —$S(O)_2$—, —$S(O)_2$O—, —$OS(O)_2$—, —$S(O)_2NR_{L3a}$—, or —$NR_{L3a}S(O)_2$—;

$R_{L3a}$ is hydrogen, $C_1$-$C_6$ alkyl optionally substituted with $R^9$, or a nitrogen protecting group;

$R_{L3b}$ is independently, at each occurrence, selected from the group consisting of hydrogen, halogen, $C_1$-$C_6$ alkyl, $C_2$-$C_6$ alkenyl, $C_2$-$C_6$ alkynyl, 3-8 membered cycloalkyl, 3-12 membered heterocycloalkyl, 6-10 membered aryl, and 5-8 membered heteroaryl, wherein alkyl, alkenyl, alkynyl, cycloalkyl, heterocyclyl, aryl, and heteroaryl are optionally substituted with one, two, or three $R^9$;

or, alternatively, two $R_{L3b}$ groups, together with the atoms to which they are attached, form a 3-8 membered cycloalkyl or 4-7 membered heterocycloalkyl, both of which are optionally substituted with one, two, or three $R^9$;

$L_4$ is a bond or $C_1$-$C_6$ alkyl optionally substituted with one, two, or three $R^9$;

each of $R_{E1}$, $R_{E2}$, $R_{E3}$, and $R_{E4}$ is independently selected from the group consisting of hydrogen, halogen, $C_1$-$C_6$ alkyl, $C_2$-$C_6$ alkenyl, $C_2$-$C_6$ alkynyl, 3-12 membered cycloalkyl, 3-12 membered heterocycloalkyl, 6-12 membered aryl, and 5-12 membered heteroaryl, CN, $CH_2OR_{EE}$, $CH_2N(R_{EE})_2$, $CH_2SR_{EE}$, $OR_{EE}$, $N(R_{EE})_2$, $SR_{EE}$, wherein alkyl, alkenyl, alkynyl, cycloalkyl, heterocyclyl, aryl, and heteroaryl are optionally substituted with one, two, or three $R^9$;

or, alternatively, $R_{E1}$ and $R_{E3}$, or $R_{E2}$ and $R_{E3}$, or $R_{E1}$ and $R_{E2}$ are joined to form 3-8 membered cycloalkyl or 4-7 membered heterocycloalkyl, both of which are optionally substituted with one, two, or three $R^9$;

each $R_{EE}$ is independently selected from the group consisting of hydrogen, $C_1$-$C_6$ alkyl, $C_1$-$C_6$ alkoxy, $C_2$-$C_6$ alkenyl, $C_2$-$C_6$ alkynyl, 3-8 membered cycloalkyl, 3-8 membered heterocycloalkyl, 6-10 membered aryl, and 5-10 membered heteroaryl, wherein alkyl, alkenyl, alkynyl, cycloalkyl, heterocyclyl, aryl, and heteroaryl are optionally substituted with one, two, or three $R^9$;

or, alternatively, two $R_{EE}$ groups, together with the atom to which they are attached, form 4-7 membered heterocycloalkyl;

$R_{E6}$ is hydrogen, $C_1$-$C_6$ alkyl, or a nitrogen protecting group;

each Y is independently O, S, $CH_2$, or N $R_{E7}$;

$R_{E7}$ is hydrogen, $C_1$-$C_6$ alkyl, or a nitrogen protecting group;

each $R^9$ is independently selected from the group consisting of halo, OH, $NH_2$, $NH(C_1$-$C_6$ alkyl), and $N(C_1$-$C_6$ alkyl$)_2$;

a is 0, 1, or 2;

z is 1, 2, or 3; and n is 0, 1, or 2.

In an embodiment, $\equiv$ is an optional double bond;

X is O;

A is $C_6$-$C_{10}$ aryl or 5-10 membered heteroaryl;

B is $C_6$-$C_{10}$ aryl or 5-10 membered heteroaryl;

$R^1$ is selected from the group consisting of H, halo, and $C_{1-6}$ alkyl, wherein alkyl is optionally substituted with $R^a$;

$R^4$ is selected from the group consisting of H, halo, OH, $NH_2$, $C_{1-6}$ alkyl, $C_{2-6}$ alkenyl, $C_{2-6}$ alkynyl, $NH(C_{1-6}$ alkyl), $N(C_{1-6}$ alkyl$)_2$, $C_{1-6}$ haloalkyl, $C_{1-6}$ alkoxy, $C_{1-6}$ alkyl-OH, $C_6$-$C_{10}$ aryl, 5-10 membered heteroaryl, $C_3$-$C_{10}$ cycloalkyl, and 3-10 membered heterocycloalkyl;

$R^5$ is selected from the group consisting of H, halo, OH, $NH_2$, $C_{1-6}$ alkyl, $C_{2-6}$ alkenyl, $C_{2-6}$ alkynyl, $NH(C_{1-6}$ alkyl), $N(C_{1-6}$ alkyl$)_2$, $C_{1-6}$ haloalkyl, $C_{1-6}$ alkoxy, $C_6$-$C_{10}$ aryl, 5-10 membered heteroaryl, $C_3$-$C_{10}$ cycloalkyl, and 3-10 membered heterocycloalkyl;

each $R^{4'}$, $R^6$, $R^{6'}$, $R^7$, $R^{7'}$, $R^8$, $R^{8'}$, $R^9$, and $R^{9'}$ is independently selected from the group consisting of H, halo, OH, $NH_2$, and $C_{1-6}$ alkyl;

$R^a$ is 3-10 membered heterocycloalkyl substituted with $C_{1-3}$ alkyl;

$R^2$ is selected from the group consisting of:

(i-1)

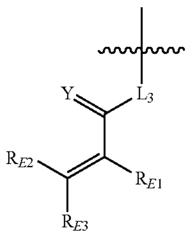

(i-2)

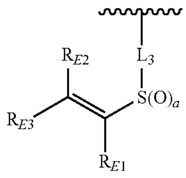

(i-3)

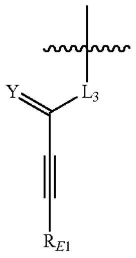

(i-4)

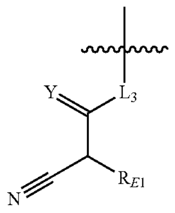

(i-9)

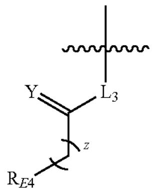

(i-11)

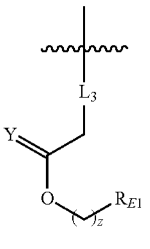

-continued (i-13)

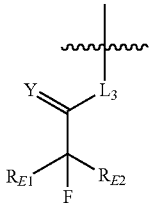

(i-14)

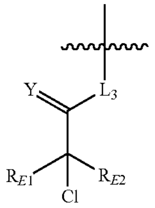

(i-18)

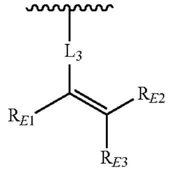

(i-19)

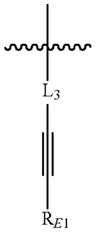

(i-28)

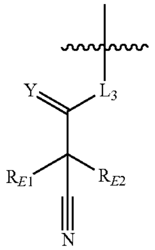

(i-36)

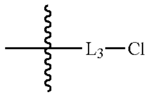

(i-37)

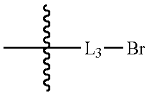

(i-38)

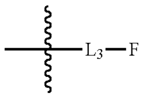

(i-39)

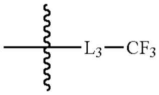

-continued (i-42)

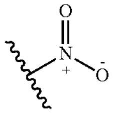

(i-43)

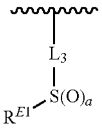

(i-44)

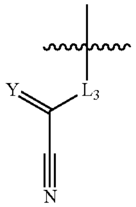

and (i-45)

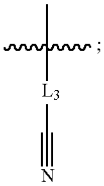

;

$L_3$ is a bond or —NH—;

each of $R_{E1}$, $R_{E2}$, $R_{E3}$, and $R_{E4}$ is independently selected from the group consisting of hydrogen, halogen, $C_1$-$C_6$ alkyl, $C_2$-$C_6$ alkenyl, $C_2$-$C_6$ alkynyl, 3-12 membered cycloalkyl, 3-12 membered heterocycloalkyl, 6-12 membered aryl, and 5-12 membered heteroaryl, CN, $CH_2OR_{EE}$, $CH_2N(R_{EE})_2$, $CH_2SR_{EE}$, $OR_{EE}$, $N(R_{EE})_2$, $SR_{EE}$, wherein alkyl, alkenyl, alkynyl, cycloalkyl, heterocyclyl, aryl, and heteroaryl are optionally substituted with one, two, or three $R^9$;

each $R_{EE}$ is independently selected from the group consisting of hydrogen, $C_1$-$C_6$ alkyl, $C_1$-$C_6$ alkoxy, $C_2$-$C_6$ alkenyl, $C_2$-$C_6$ alkynyl, 3-8 membered cycloalkyl, 3-8 membered heterocycloalkyl, 6-10 membered aryl, and 5-10 membered heteroaryl, wherein alkyl, alkenyl, alkynyl, cycloalkyl, heterocyclyl, aryl, and heteroaryl are optionally substituted with one, two, or three $R^9$;

each Y is independently O, S, $CH_2$, or $NR_{E7}$;

$R_{E7}$ is hydrogen, $C_1$-$C_6$ alkyl, or a nitrogen protecting group;

each $R^9$ is independently selected from the group consisting of halo, OH, $NH_2$, $NH(C_1$-$C_6$ alkyl), and $N(C_1$-$C_6$ alkyl$)_2$;

a is 0, 1, or 2;

z is 1, 2, or 3; and n is 0, 1, or 2.

In an embodiment, the compound of Formula I is a compound of Formula II:

(II)

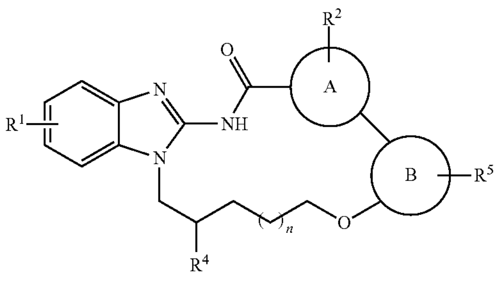

or a pharmaceutically acceptable salt thereof.

In another embodiment,

A is phenyl or 5-10 membered heteroaryl;

B is phenyl or 5-10 membered heteroaryl;

$R^1$ is selected from the group consisting of H, halo, and $C_{1-6}$ alkyl, wherein alkyl is optionally substituted with $R^a$;

$R^4$ is $C_{1-6}$ alkyl;

$R^5$ is H or $C_{1-8}$ alkyl;

$R^a$ is 5-6 membered heterocycloalkyl substituted with $C_{1-3}$ alkyl;

$R^2$ is (i-1)

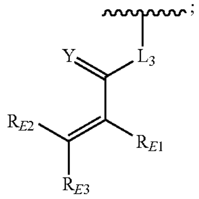

wherein $L_3$ is a bond or —NH—;

each of $R_{e1}$, $R_{E2}$, and $R_{E3}$ is independently selected from the group consisting of hydrogen, halogen, and $C_1$-$C_6$ alkyl;

Y is O or $CH_2$; and n is 0, 1, or 2.

In yet another embodiment, A is selected from the group consisting of phenyl, 5-6 membered heteroaryl, $C_3$-$C_8$ cycloalkyl, and 3-8 membered heterocycloalkyl. In still another embodiment, A is $C_6$-$C_{10}$ aryl. In an embodiment, A is 5-6 membered heteroaryl. In another embodiment, A is $C_3$-$C_8$ cycloalkyl. In yet another embodiment, A is 3-8 membered heterocycloalkyl.

In still another embodiment, A is phenyl or thiophene. In another embodiment, A is phenyl. In another embodiment, A is thiophene.

In an embodiment, B is selected from the group consisting of phenyl, 5-6 membered heteroaryl, $C_3$-$C_8$ cycloalkyl, and 3-8 membered heterocycloalkyl. In another embodiment, B is 5-6 membered heteroaryl. In yet another embodiment, B is $C_3$-$C_8$ cycloalkyl. In still another embodiment, B is 3-8 membered heterocycloalkyl.

In an embodiment, B is selected from the group consisting of phenyl, pyridine, pyrazole, pyridazine, and pyrimidine. In another embodiment, B is phenyl. In yet another embodiment, B is pyridine. In still another embodiment, B is pyrazole. In an embodiment, B is pyridazine. In another embodiment, B is pyrimidine.

In yet another embodiment, $R^1$ is selected from the group consisting of H, halo, $C_{1-6}$ alkyl, NH($C_{1-6}$ alkyl), N($C_{1-6}$ alkyl)$_2$, $C_{1-6}$ haloalkyl, and $C_{1-6}$ alkoxy, wherein $C_{1-6}$ alkyl is substituted with $R^a$.

In still another embodiment, $R^1$ is selected from the group consisting of H, halo, $C_{1-6}$ alkyl, $C_{1-6}$ haloalkyl, and $C_{1-6}$ alkoxy, wherein $C_{1-6}$ alkyl is substituted with $R^a$. In an embodiment, $R^1$ is H, halo, or $C_{1-6}$ alkyl substituted with $R^a$. In another embodiment, $R^1$ is H.

In yet another embodiment, $R^1$ is $C_{1-6}$ alkyl substituted with $R^a$. In still another embodiment, $R^1$ is halo.

In an embodiment, $R^a$ is selected from the group consisting of $C_6$-$C_{10}$ aryl, 5-9 membered heteroaryl, $C_3$-$C_8$ cycloalkyl, and 3-8 membered heterocycloalkyl all of which are optionally substituted with $C_{1-3}$ alkyl. In another embodiment, $R^a$ is 4-8 membered heterocycloalkyl substituted with methyl. In yet another embodiment, $R^a$ is piperazine substituted with methyl.

In another embodiment, $R^4$ is selected from the group consisting of H, $C_{1-6}$ alkyl, $C_2$-6 alkenyl, $C_{2-6}$ alkynyl, $C_{1-6}$ haloalkyl, and $C_{1-6}$ alkoxy. In yet another embodiment, $R^4$ is H or $C_{1-6}$ alkyl. In still another embodiment, $R^4$ is H. In an embodiment, $R^4$ is $C_{1-8}$ alkyl. In another embodiment, $R^4$ is methyl.

In yet another embodiment, $R^5$ is selected from the group consisting of H, halo, OH, $NH_2$, $C_{1-6}$ alkyl, $C_{2-6}$ alkenyl, $C_{2-6}$ alkynyl, NH($C_{1-6}$ alkyl), N($C_{1-6}$ alkyl)$_2$, $C_{1-8}$ haloalkyl, and $C_{1-6}$ alkoxy. In still another embodiment, $R^5$ is H or $C_{1-6}$ alkyl. In an embodiment, $R^5$ is H. In another embodiment, $R^5$ is $C_{1-6}$ alkyl.

In an embodiment, each $R^6$, $R^{6'}$, $R^7$, $R^{7'}$, $R^8$, $R^{8'}$, $R^9$, and $R^{9'}$ is H.

In an embodiment, $R^{4'}$ is H and $R^4$ is H or $C_{1-6}$ alkyl.

In another embodiment, $R^2$ is selected from the group consisting of (i-1)

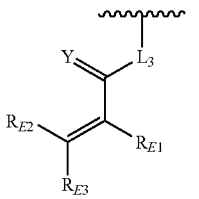

(i-2)

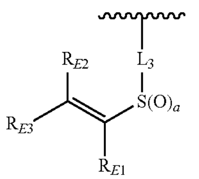

(i-3)

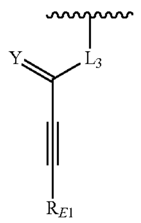

-continued
(i-14)
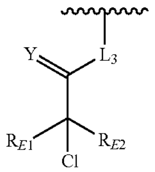
(i-13)
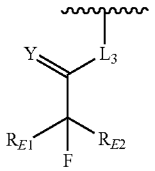
(i-19)
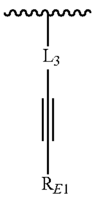 and
(i-43)
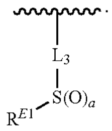
In yet another embodiment, $R^2$ is selected from the group consisting of
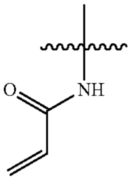
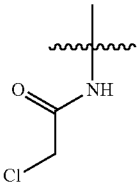
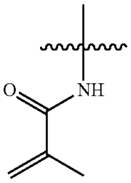
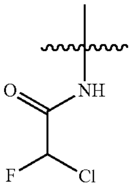
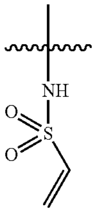
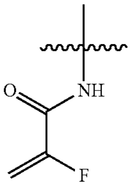
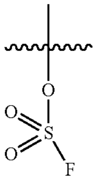
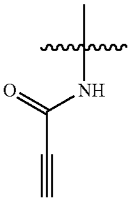
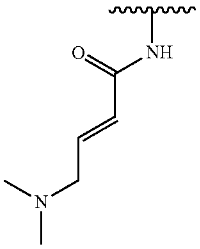
-continued
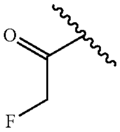
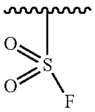
and
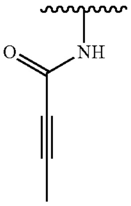
.
In another embodiment, $R^2$ is selected from the group consisting of
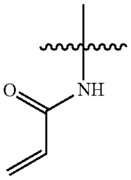
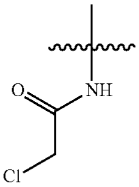
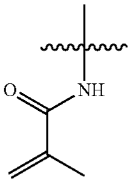
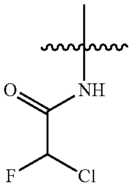
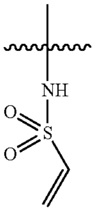
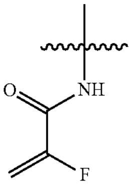
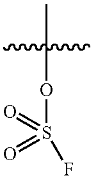
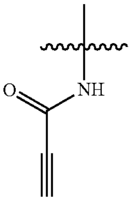
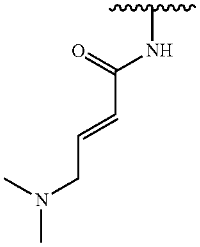
and
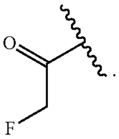
In still another embodiment, $R^2$ is
(i-1)
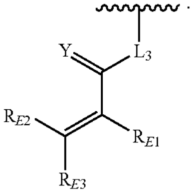
In an embodiment, $R^2$ is
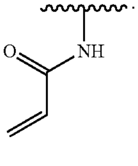 [SMILES: *NC(=O)C=C]

In another embodiment, the compound of Formula I is selected from the group consisting of:
| Compound No. | Structure |
|---|---|
| 001 | 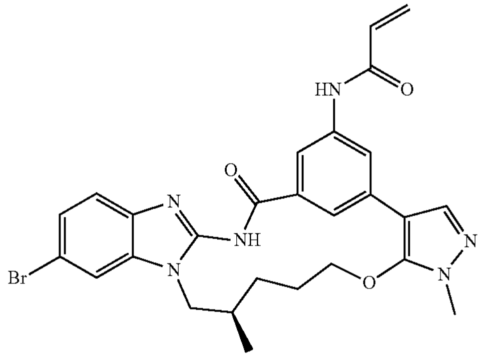 [SMILES: C=CC(=O)Nc1cc2cc(c1)-c1cnn(C)c1OCCC[C@@H](C)Cn1c(nc3ccc(Br)cc31)NC2=O] |
| 002 | 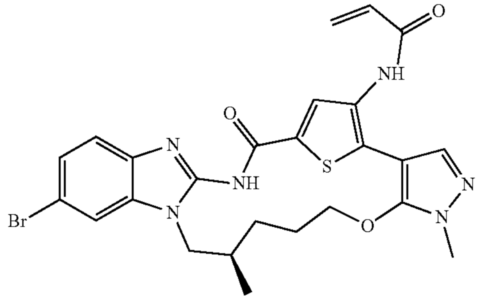 [SMILES: C=CC(=O)NC1=C2SC(=C1)C(=O)Nc1nc3ccc(Br)cc3n1C[C@H](C)CCCOc1c2cnn1C] |
| 003 | 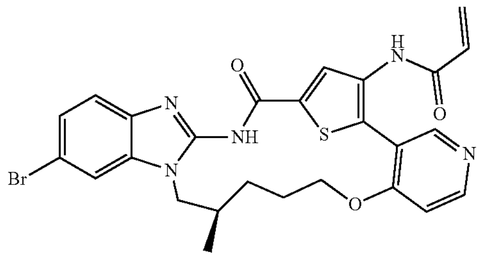 [SMILES: C=CC(=O)NC1=C2SC(=C1)C(=O)Nc1nc3ccc(Br)cc3n1C[C@H](C)CCCOc1ccncc12] |
| 004 | 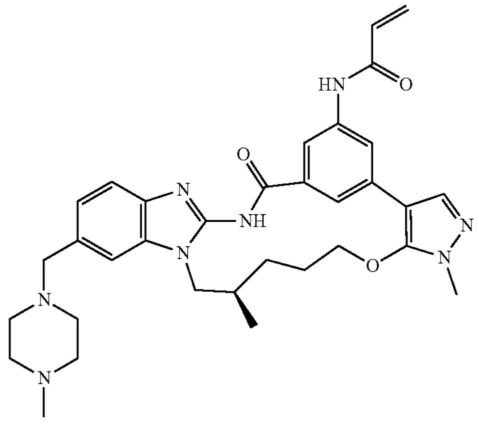 [SMILES: C=CC(=O)Nc1cc2cc(c1)-c1cnn(C)c1OCCC[C@@H](C)Cn1c(nc3ccc(CN4CCN(C)CC4)cc31)NC2=O] |
-continued
| Compound No. | Structure |
|---|---|
| 005 | 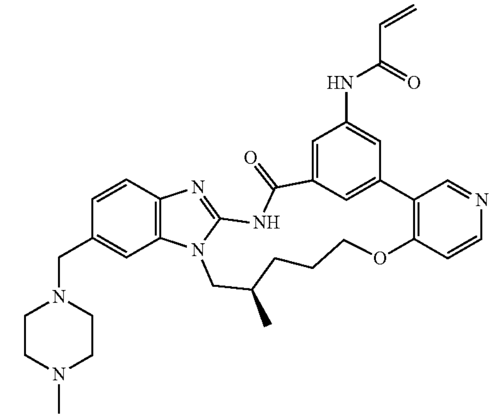 [SMILES: C=CC(=O)Nc1cc2cc(c1)-c1cnccc1OCCC[C@@H](C)Cn1c(nc3ccc(CN4CCN(C)CC4)cc31)NC2=O] |
| 006 | 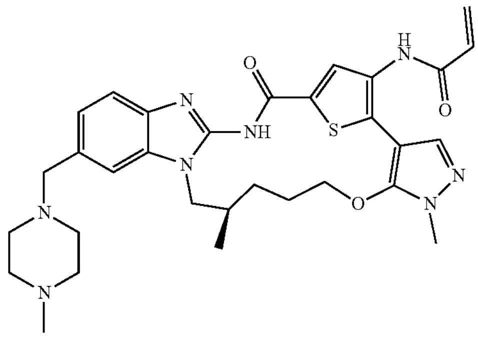 [SMILES: C=CC(=O)NC1=C2SC(=C1)C(=O)Nc1nc3ccc(CN4CCN(C)CC4)cc3n1C[C@H](C)CCCOc1c2cnn1C] |
| 007 | 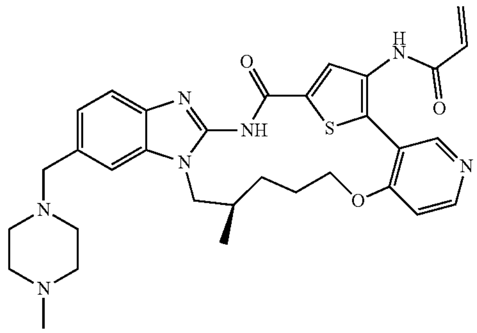 [SMILES: C=CC(=O)NC1=C2SC(=C1)C(=O)Nc1nc3ccc(CN4CCN(C)CC4)cc3n1C[C@H](C)CCCOc1ccncc12] |
| 008 | 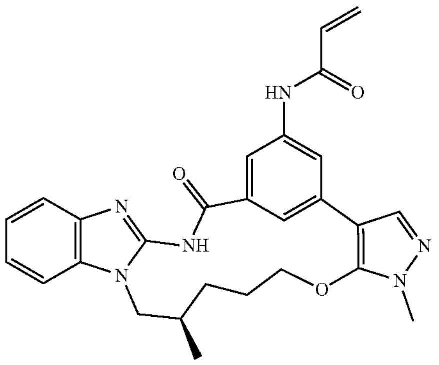 [SMILES: C=CC(=O)Nc1cc2cc(c1)-c1cnn(C)c1OCCC[C@@H](C)Cn1c(nc3ccccc31)NC2=O] |

-continued

| Compound No. | Structure |
| --- | --- |
| 009 | 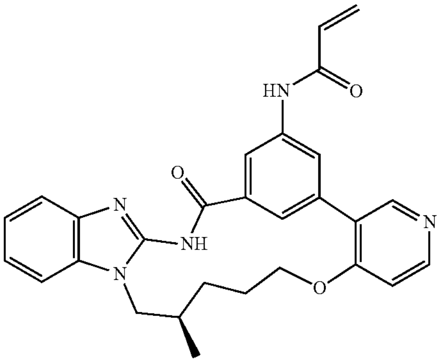 [SMILES: C=CC(=O)Nc1cc2cc(c1)-c1cnccc1OCCC[C@@H](C)Cn1c(nc3ccccc31)NC2=O] |
| 010 | 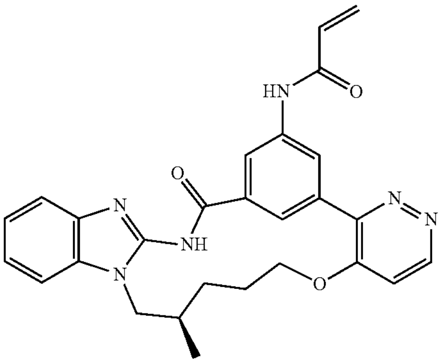 [SMILES: C=CC(=O)Nc1cc2cc(c1)-c1nnccc1OCCC[C@@H](C)Cn1c(nc3ccccc31)NC2=O] |
| 011 | 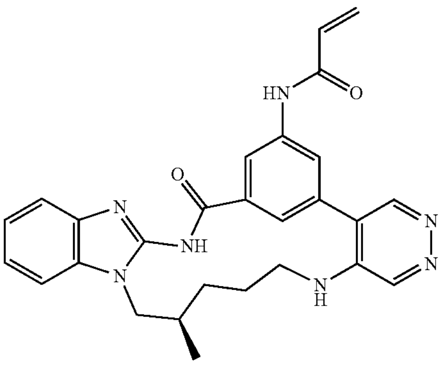 [SMILES: C=CC(=O)Nc1cc2cc(c1)-c1cnncc1NCCC[C@@H](C)Cn1c(nc3ccccc31)NC2=O] |
| 012 | 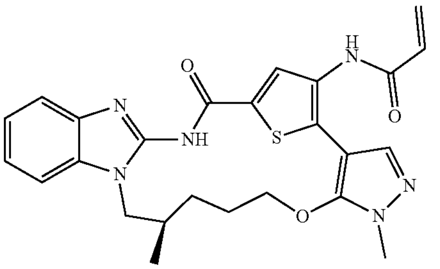 [SMILES: C=CC(=O)NC1=C2SC(=C1)C(=O)Nc1nc3ccccc3n1C[C@H](C)CCCOc1c2cnn1C] |
| 013 | 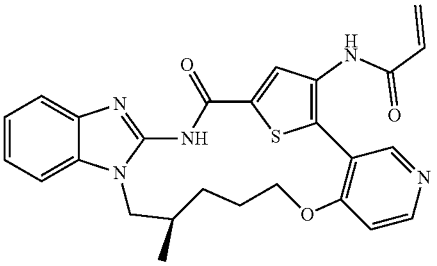 [SMILES: C=CC(=O)NC1=C2SC(=C1)C(=O)Nc1nc3ccccc3n1C[C@H](C)CCCOc1ccncc12] |
| 014 | 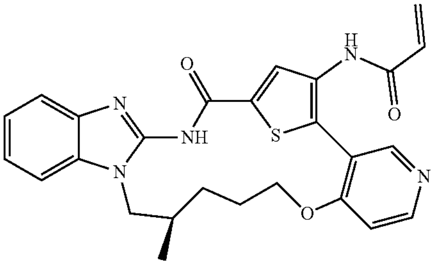 [SMILES: C=CC(=O)NC1=C2SC(=C1)C(=O)Nc1nc3ccccc3n1C[C@H](C)CCCOc1ccncc12] |
| 015 | 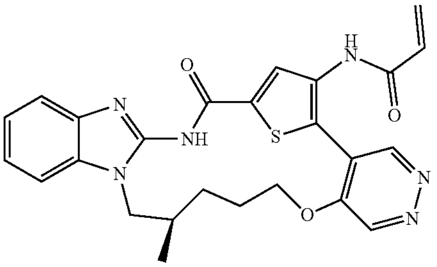 [SMILES: C=CC(=O)NC1=C2SC(=C1)C(=O)Nc1nc3ccccc3n1C[C@H](C)CCCOc1cnncc12] |

or a pharmaceutically acceptable salt thereof.

In an embodiment of Formulae I and II,

X is O;

A is 5-6 membered heteroaryl;

B is 5-6 membered heteroaryl;

$R^1$ is H or halo;

$R^4$ is $C_{1-3}$ alkyl;

$R^5$ is H or $C_{1-3}$ alkyl; and $R^2$ is

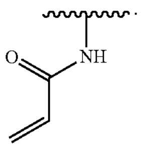

In another embodiment of Formulae I and II,

X is O;

A is 5-6 membered heteroaryl;

B is 5-6 membered heteroaryl;

$R^1$ is halo or $C_{1-3}$ alkyl substituted with Ra;

$R^4$ is $C_{1-3}$ alkyl;

$R^5$ is H or $C_{1-3}$ alkyl;

$R^a$ is 3-7 membered heterocycloalkyl substituted with methyl; and $R^2$ is

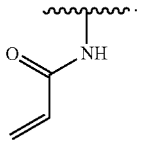 [SMILES: *NC(=O)C=C]

The compounds disclosed herein may exist as tautomers and optical isomers (e.g., enantiomers, diastereomers, diastereomeric mixtures, racemic mixtures, and the like).

It is generally well known in the art that any compound that will be converted in vivo to provide a compound disclosed herein is a prodrug within the scope of the present disclosure.

Compounds provided herein can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

In the compounds provided herein, any atom not specifically designated as a particular isotope is meant to represent any stable isotope of that atom. Unless otherwise stated, when a position is designated specifically as "H" or "hydrogen," the position is understood to have hydrogen at its natural abundance isotopic composition. Also, unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

In embodiments, the compounds provided herein have an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In an aspect, provided herein is a pharmaceutical composition comprising any one of the compounds disclosed herein, or a pharmaceutically acceptable salt thereof, and at least one pharmaceutically acceptable carrier.

In another aspect, provided herein is a method of inhibiting the activity of EGFR, comprising administering to a subject in need thereof an effective amount of a compound of disclosed herein or a pharmaceutical composition comprising a compound disclosed herein and a pharmaceutically acceptable carrier. In an embodiment, the compound targets Cys775 on EGFR.

In an embodiment, the composition further comprises a second active agent. In another embodiment, the second active agent is selected from the group consisting of a MEK inhibitor, a PI3K inhibitor, and an mTor inhibitor. In yet another embodiment, the second active agent prevents EGFR dimer formation in a subject. In still another embodiment, the second active agent is selected from the group consisting of cetuximab, trastuzumab, and panitumumab. In an embodiment, the second active agent is an ATP competitive EGFR inhibitor. In another embodiment, the ATP competitive EGFR inhibitor is osimertinib, gefitinib, or erlotinib. In another embodiment, the ATP competitive EGFR inhibitor is osimertinib.

In another aspect, provided herein are pharmaceutical compositions comprising a compound of the present disclosure, or a pharmaceutically acceptable salt thereof, and a pharmaceutically acceptable carrier. In another aspect, the pharmaceutical composition further comprises a second active agent, wherein said second active agent prevents EGFR dimer formation, and a pharmaceutically acceptable carrier. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab.

A compound that binds to an allosteric site in EGFR, such as the compounds of the present disclosure (e.g., the compounds of the formulae disclosed herein), optionally in combination with a second active agent, wherein said second active agent prevents EGFR dimer formation, are capable of modulating EGFR activity. In some embodiments, the compounds of the present disclosure are capable of inhibiting or decreasing EGFR activity without a second active agent (e.g., an antibody such as cetuximab, trastuzumab, or panitumumab). In other embodiments, the compounds of the present disclosure in combination with a second active agent. In an embodiment, the second active agent prevents EGFR dimer formation and/or are capable of inhibiting or decreasing EGFR activity. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

Methods of Treatment

In an aspect, provided herein is a method of treating cancer in an individual in need thereof, comprising administering to the individual a therapeutically effective amount of a compound disclosed herein. In an embodiment, the cancer is selected from the group consisting of lung cancer, colon cancer, breast cancer, endometrial cancer, thyroid cancer, glioma, squamous cell carcinoma, and prostate cancer. In another embodiment, the cancer is non-small cell lung cancer (NSCLC).

In another aspect, provided herein is a method of inhibiting a kinase in an individual in need thereof, comprising administering to the individual a therapeutically effective amount of a compound provided herein. In an embodiment, the kinase is EGFR.

In yet another aspect, provided herein is a method of treating or preventing a kinase-mediated disorder in an individual in need thereof, comprising administering to the individual a therapeutically effective amount of a compound of the present disclosure. In an embodiment, the kinase-mediated disorder is resistant to an EGFR-targeted therapy. In another embodiment, the EGFR-treated therapy is selected from the group consisting of gefitinib, erlotinib, osimertinib, CO-1686, and WZ4002.

In some embodiments, the compounds of the present disclosure are capable of modulating (e.g., inhibiting or decreasing) the activity of EGFR containing one or more mutations. In some embodiments, the mutant EGFR contains one or more mutations selected from T790M, L718Q, L844V, V948R, L858R, 1941 R, $C_{797}S$, and Del. In other embodiments, the mutant EGFR contains a combination of mutations, wherein the combination is selected from Del/L718Q, Del/L844V, Del/T790M, Del/T790M/L718Q, Del/T790M/L844V, L858R/L718Q, L858R/L844V, L858R/T790M, L858R/T790M/I941R, Del/T790M, Del/T790M/$C_{797}S$, L858R/T790M/$C_{797}S$, and L858R/T790M/L718Q. In other embodiments, the mutant EGFR contains a combination of mutations, wherein the combination is selected from Del/L844V, L858R/L844V, L858R/T790M, L858R/T790M/I941R, L858R/T790M/$C_{797}S$, Del/T790M, Del/T790M, Del/T790M/$C_{797}S$, and L858R/T790M. In other embodiments, the mutant EGFR contains a combination of mutations, wherein the combination is selected from L858R/T790M, L858R/T790M/I941R, L858R/T790M/$C_{797}S$, Del/T790M, Del/T790M/$C_{797}S$, and L858R/T790M.

In some embodiments, the compounds of the present disclosure in combination with a second active agent, wherein said second active agent prevents EGFR dimer formation, are capable of modulating (e.g., inhibiting or decreasing) the activity of EGFR containing one or more mutations. In some embodiments, the mutant EGFR contains one or more mutations selected from T790M, L718Q, L844V, V948R, L858R, I941R, $C_{797}S$, and Del. In other embodiments, the mutant EGFR contains a combination of mutations, wherein the combination is selected from Del/L718Q, Del/L844V, Del/T790M, Del/T790M/L718Q, Del/T790M/L844V, L858R/L718Q, L858R/L844V, L858R/T790M, L858R/T790M/I941R, Del/T790M, Del/T790M/$C_{797}S$, L858R/T790M/$C_{797}S$, and L858R/T790M/L718Q. In other embodiments, the mutant EGFR contains a combination of mutations, wherein the combination is selected from Del/L844V, L858R/L844V, L858R/T790M, L858R/T790M/I941R, L858R/T790M/$C_{797}S$, Del/T790M, Del/T790M/$C_{797}S$, and L858R/T790M. In other embodiments, the mutant EGFR contains a combination of mutations, wherein the combination is selected from L858R/T790M, L858R/T790M/I941R, L858R/T790M/$C_{797}S$, Del/T790M, Del/T790M/$C_{797}S$, and L858R/T790M. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib.

In some embodiments, the compounds of the present disclosure are capable of modulating (e.g., inhibiting or decreasing) the activity of EGFR containing one or more mutations, but do not affect the activity of a wild-type EGFR.

In other embodiments, the compounds of the present disclosure in combination with a second active agent, wherein said second active agent prevents EGFR dimer formation, are capable of modulating (e.g., inhibiting or decreasing) the activity of EGFR containing one or more mutations, but do not affect the activity of a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

Modulation of EGFR containing one or more mutations, such as those described herein, but not a wild-type EGFR, provides an approach to the treatment, prevention, or amelioration of diseases including, but not limited to, cancer and metastasis, inflammation, arthritis, systemic lupus erythematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy.

In some embodiments, the compounds of the disclosure exhibit greater inhibition of EGFR containing one or more mutations as described herein relative to a wild-type EGFR. In certain embodiments, the compounds of the disclosure exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds of the disclosure exhibit up to 1000-fold greater inhibition of EGFR containing one or more mutations as described herein relative to a wild-type EGFR. In various embodiments, the compounds of the disclosure exhibit up to 10000-fold greater inhibition of EGFR having a combination of mutations described herein (e.g., L858R/T790M, L858R/T790M/I941R, L858R/T790M/$C_{797}S$, Del/T790M, Del/T790M/$C_{797}S$, and L858R/T790M) relative to a wild-type EGFR.

In other embodiments, the compounds of the disclosure in combination with a second active agent, wherein said second active agent prevents EGFR dimer formation, exhibit greater inhibition of EGFR containing one or more mutations as described herein relative to a wild-type EGFR. In certain embodiments, the compounds of the disclosure in combination with a second active agent, wherein said second active agent prevents EGFR dimer formation, exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds of the disclosure in combination with a second active agent, wherein said second active agent prevents EGFR dimer formation, exhibit up to 1000-fold greater inhibition of EGFR containing one or more mutations as described herein relative to a wild-type EGFR. In various embodiments, the compounds of the disclosure in combination with a second active agent, wherein said second active agent prevents EGFR dimer formation, exhibit up to 10000-fold greater inhibition of EGFR having a combination of mutations described herein (e.g., L858R/T790M, L858R/T790M/I941R, L858R/T790M/$C_{797}$S, Del/T790M, Del/T790M/$C_{797}$S, and L858R/T790M) relative to a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In some embodiments, the compounds of the disclosure exhibit from about 2-fold to about 10-fold greater inhibition of EGFR containing one or more mutations as described herein relative to a wild-type EGFR. In various embodiments, the compounds of the disclosure exhibit from about 10-fold to about 100-fold greater inhibition of EGFR containing one or more mutations as described herein relative to a wild-type EGFR. In various embodiments, the compounds of the disclosure exhibit from about 100-fold to about 1000-fold greater inhibition of EGFR containing one or more mutations as described herein relative to a wild-type EGFR. In various embodiments, the compounds of the disclosure exhibit from about 1000-fold to about 10000-fold greater inhibition of EGFR containing one or more mutations as described herein relative to a wild-type EGFR.

In other embodiments, the compounds of the disclosure in combination with a second active agent, wherein said second active agent prevents EGFR dimer formation, exhibit from about 2-fold to about 10-fold greater inhibition of EGFR containing one or more mutations as described herein relative to a wild-type EGFR. In other embodiments, the compounds of the disclosure in combination with a second active agent, wherein said second active agent prevents EGFR dimer formation, exhibit from about 10-fold to about 100-fold greater inhibition of EGFR containing one or more mutations as described herein relative to a wild-type EGFR. In other embodiments, the compounds of the disclosure in combination with a second active agent wherein said second active agent prevents EGFR dimer formation exhibit from about 100-fold to about 1000-fold greater inhibition of EGFR containing one or more mutations as described herein relative to a wild-type EGFR. In other embodiments, the compounds of the disclosure in combination with a second active agent, wherein said second active agent prevents EGFR dimer formation, exhibit from about 1000-fold to about 10000-fold greater inhibition of EGFR containing one or more mutations as described herein relative to a wild-type EGFR. In other embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In certain embodiments, the compounds of the disclosure exhibit at least 2-fold greater inhibition of EGFR having a combination of mutations selected from L858R/T790M, L858R/T790M/I941R, L858R/T790M/$C_{797}$S, Del/T790M, Del/T790M/$C_{797}$S, and L858R/T790M relative to a wild-type EGFR. In certain embodiments, the compounds of the disclosure exhibit at least 3-fold greater inhibition of EGFR having a combination of mutations selected from L858R/T790M, L858R/T790M/I941R, L858R/T790M/$C_{797}$S, Del/T790M, Del/T790M/$C_{797}$S, and L858R/T790M relative to a wild-type EGFR. In certain embodiments, the compounds of the disclosure exhibit at least 5-fold greater inhibition of EGFR having a combination of mutations selected from L858R/T790M, L858R/T790M/I941R, L858R/T790M/$C_{797}$S, Del/T790M, Del/T790M/$C_{797}$S, and L858R/T790M relative to a wild-type EGFR. In certain embodiments, the compounds of the disclosure exhibit at least 10-fold greater inhibition of EGFR having a combination of mutations selected from L858R/T790M, L858R/T790M/I941R, L858R/T790M/$C_{797}$S, Del/T790M, Del/T790M/$C_{797}$S, and L858R/T790M relative to a wild-type EGFR. In certain embodiments, the compounds of the disclosure exhibit at least 25-fold greater inhibition of EGFR having a combination of mutations selected from L858R/T790M, L858R/T790M/I941R, L858R/T790M/$C_{797}$S, Del/T790M, Del/T790M/$C_{797}$S, and L858R/T790M relative to a wild-type EGFR. In certain embodiments, the compounds of the disclosure exhibit at least 50-fold greater inhibition of EGFR having a combination of mutations selected from L L858R/T790M, L858R/T790M/I941R, L858R/T790M/$C_{797}$S, Del/T790M, Del/T790M/$C_{797}$S, and L858R/T790M relative to a wild-type EGFR. In certain embodiments, the compounds of the disclosure exhibit at least 100-fold greater inhibition of EGFR having a combination of mutations selected from L858R/T790M, L858R/T790M/I941R, L858R/T790M/$C_{797}$S, Del/T790M, Del/T790M/$C_{797}$S, and L858R/T790M relative to a wild-type EGFR.

In certain embodiments, the compounds of the disclosure in combination with a second active agent, wherein said second active agent prevents EGFR dimer formation, exhibit at least 2-fold greater inhibition of EGFR having a combination of mutations selected from L858R/T790M, L858R/T790M/I941R, L858R/T790M/$C_{797}$S, Del/T790M, Del/T790M/$C_{797}$S, and L858R/T790M relative to a wild-type EGFR. In certain embodiments, the compounds of the disclosure in combination with a second active agent, wherein said second active agent prevents EGFR dimer formation, exhibit at least 3-fold greater inhibition of EGFR having a combination of mutations selected from L858R/T790M, L858R/T790M/I941R, L858R/T790M/$C_{797}$S, Del/T790M, Del/T790M/$C_{797}$S, and L858R/T790M relative to a wild-type EGFR. In certain embodiments, the compounds of the disclosure in combination with a second active agent, wherein said second active agent prevents EGFR dimer formation, exhibit at least 5-fold greater inhibition of EGFR having a combination of mutations selected from L858R/T790M, L858R/T790M/I941R, L858R/T790M/$C_{797}$S, Del/T790M, Del/T790M/$C_{797}$S, and L858R/T790M relative to a wild-type EGFR. In certain embodiments, the compounds of the disclosure in combination with a second active agent, wherein said second active agent prevents EGFR dimer formation, exhibit at least 10-fold greater inhibition of EGFR having a combination of mutations selected from L858R/T790M, L858R/T790M/I941R, L858R/T790M/

$C_{797}S$, Del/T790M, Del/T790M/$C_{797}S$, and L858R/T790M relative to a wild-type EGFR. In certain embodiments, the compounds of the disclosure in combination with a second active agent, wherein said second active agent prevents EGFR dimer formation, exhibit at least 25-fold greater inhibition of EGFR having a combination of mutations selected from L858R/T790M, L858R/T790M/I941R, L858R/T790M/$C_{797}S$, Del/T790M, Del/T790M/$C_{797}S$, and L858R/T790M relative to a wild-type EGFR. In certain embodiments, the compounds of the disclosure in combination with a second active agent, wherein said second active agent prevents EGFR dimer formation, exhibit at least 50-fold greater inhibition of EGFR having a combination of mutations selected from L L858R/T790M, L858R/T790M/I941R, L858R/T790M/$C_{797}S$, Del/T790M, Del/T790M/$C_{797}S$, and L858R/T790M relative to a wild-type EGFR. In certain embodiments, the compounds of the disclosure in combination with a second active agent, wherein said second active agent prevents EGFR dimer formation, exhibit at least 100-fold greater inhibition of EGFR having a combination of mutations selected from L858R/T790M, L858R/T790M/I941R, L858R/T790M/$C_{797}S$, Del/T790M, Del/T790M/$C_{797}S$, and L858R/T790M relative to a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In some embodiments, the inhibition of EGFR activity is measured by $IC_{50}$.

In some embodiments, the inhibition of EGFR activity is measured by $EC_{50}$.

In some embodiments, the inhibition of EGFR by a compound of the disclosure can be measured via a biochemical assay. By illustrative and non-limiting example, a homogenous time-resolved fluorescence (HTRF) assay may be used to determine inhibition of EGFR activity using conditions and experimental parameters disclosed herein. The HTRF assay may, for example, employ concentrations of substrate (e.g., biotin-Lck-peptide substrate) of about 1 μM; concentrations of EGFR (mutant or WT) from about 0.2 nM to about 40 nM; and concentrations of inhibitor from about 0.000282 μM to about 50 μM. A compound of the disclosure screened under these conditions may, for example, exhibit an $IC_{50}$ value from about 1 nM to >1 μM; from about 1 nM to about 400 nM; from about 1 nM to about 150 nM; from about 1 nM to about 75 nM; from about 1 nM to about 40 nM; from about 1 nM to about 25 nM; from about 1 nM to about 15 nM; or from about 1 nM to about 10 nM. In certain embodiments, a compound of the disclosure screened under the above conditions for inhibition of EGFR having a mutation or combination of mutations selected from L858R/T790M, L858R, and T790M may, for example, exhibit an $IC_{50}$ value from about 1 nM to >1 μM; from about 1 nM to about 400 nM; from about 1 nM to about 150 nM; from about 1 nM to about 75 nM; from about 1 nM to about 40 nM; from about 1 nM to about 25 nM; from about 1 nM to about 15 nM; or from about 1 nM to about 10 nM.

In some embodiments, the compounds of the disclosure bind to an allosteric site in EGFR. In some embodiments, the compounds of the disclosure interact with at least one amino acid residue of epidermal growth factor receptor (EGFR) selected from Lys745, Leu788, and Ala 743. In other embodiments, the compounds of the disclosure interact with at least one amino acid residue of epidermal growth factor receptor (EGFR) selected from Cys775, Leu777, Phe856, and Asp855. In other embodiments, the compounds of the disclosure interact with at least one amino acid residue of epidermal growth factor receptor (EGFR) selected from Met766, 11e759, Glu762, and Ala763. In other embodiments, the compounds of the disclosure interact with at least one amino acid residue of epidermal growth factor receptor (EGFR) selected from Lys745, Leu788, and Ala 743; at least one amino acid residue of epidermal growth factor receptor (EGFR) selected from Cys775, Leu777, Phe856, and Asp855; and at least one amino acid residue of epidermal growth factor receptor (EGFR) selected from Met766, 11e759, Glu762, and Ala763. In other embodiments, the compounds of the disclosure do not interact with any of the amino acid residues of epidermal growth factor receptor (EGFR) selected from Met793, Gly796, and Cys797.

In some embodiments, the disclosure provides a compound comprising an allosteric kinase inhibitor, wherein the compound is a more potent inhibitor of a drug-resistant EGFR mutant relative to a wild type EGFR. For example, the compound can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug -resistant EGFR mutant is resistant to one or more known EGFR inhibitors, including but not limited to gefitinib, erlotinib, lapatinib, WZ4002, HKI-272, CL-387785, and osimertinib.

In some embodiments, the drug-resistant EGFR mutant comprises a sensitizing mutation, such as Del and L858R.

In some embodiments, the disclosure provides a compound comprising an allosteric kinase inhibitor in combination with a second active agent, wherein said second active agent prevents EGFR dimer formation, wherein the compound is a more potent inhibitor of a drug-resistant EGFR mutant relative to a wild type EGFR. For example, the compound in combination with a second active agent, wherein said second active agent prevents EGFR dimer formation, can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002, HKI-272, CL-387785, and osimertinib. In some embodiments, the drug-resistant EGFR mutant comprises a sensitizing mutation, such as Del and L858R. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib.

In some embodiments, the disclosure provides a compound comprising an allosteric kinase inhibitor, wherein the compound inhibits kinase activity of a drug-resistant EGFR mutant harboring a sensitizing mutation (e.g., Del and L858R) and a drug-resistance mutation (e.g., T790M, L718Q, $C_{797}S$, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold.

In other embodiments, the disclosure provides a compound comprising an allosteric kinase inhibitor in combination with a second active agent , wherein said second active agent prevents EGFR dimer formation, wherein the compound in combination with the second active agent inhibits kinase activity of a drug-resistant EGFR mutant harboring a sensitizing mutation (e.g., Del and L858R) and a drug-resistance mutation (e.g., T790M, L718Q, $C_{797}$S, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In some embodiments, the disclosure provides a compound comprising an allosteric kinase inhibitor, wherein the compound is more potent than one or more known EGFR inhibitors, including but not limited to gefitinib, erlotinib, lapatinib, WZ4002, HKI-272, CL-387785, and osimertinib, at inhibiting the activity of EGFR containing one or more mutations as described herein, such as T790M, L718Q, L844V, L858R, $C_{797}$S, and Del. For example, the compound can be at least about 2-fold, 3-fold, 5-fold, 10-fold, 25-fold, 50-fold or about 100-fold more potent (e.g., as measured by $IC_{50}$) than gefitinib, erlotinib, lapatinib, WZ4002, HKI-272, CL-387785, and osimertinib at inhibiting the activity of the EGFR containing one or more mutations as described herein.

In other embodiments, the disclosure provides a compound comprising an allosteric kinase inhibitor in combination with a second active agent , wherein said second active agent prevents EGFR dimer formation, wherein the compound in combination with the second active agent is more potent than one or more known EGFR inhibitors, including but not limited to gefitinib, erlotinib, lapatinib, WZ4002, HKI-272, CL-387785, and osimertinib, at inhibiting the activity of EGFR containing one or more mutations as described herein, such as T790M, L718Q, L844V, L858R, $C_{797}$S, and Del. For example, the compound in combination with a second active agent, wherein said second active agent prevents EGFR dimer formation, can be at least about 2-fold, 3-fold, 5-fold, 10-fold, 25-fold, 50-fold or about 100-fold more potent (e.g., as measured by $IC_{50}$) than gefitinib, erlotinib, lapatinib, WZ4002, HKI-272, CL-387785, and osimertinib at inhibiting the activity of the EGFR containing one or more mutations as described herein. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In some embodiments, the disclosure provides a compound comprising an allosteric kinase inhibitor, wherein the compound is less potent than one or more known EGFR inhibitors, including but not limited to gefitinib, erlotinib, lapatinib, WZ4002, HKI-272, CL-387785, and osimertinib, at inhibiting the activity of a wild-type EGFR. For example, the compound can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387785, and osimertinib, at inhibiting the activity of a wild-type EGFR.

In other embodiments, the disclosure provides a compound comprising an allosteric kinase inhibitor in combination with a second active agent, wherein said second active agent prevents EGFR dimer formation, wherein the compound in combination with the second active agent is less potent than one or more known EGFR inhibitors, including but not limited to gefitinib, erlotinib, lapatinib, WZ4002, HKI-272, CL-387785, and osimertinib, at inhibiting the activity of a wild-type EGFR. For example, the compound in combination with a second active agent, wherein said second active agent prevents EGFR dimer formation can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387785, and osimertinib, at inhibiting the activity of a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

Potency of the inhibitor can be determined by $EC_{50}$ value. A compound with a lower $EC_{50}$ value, as determined under substantially similar conditions, is a more potent inhibitor relative to a compound with a higher $EC_{50}$ value. In some embodiments, the substantially similar conditions comprise determining an EGFR-dependent phosphorylation level, in vitro or in vivo (e.g., in 3T3 cells expressing a wild type EGFR, a mutant EGFR, or a fragment of any thereof).

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining an EGFR-dependent phosphorylation level, in vitro or in vivo (e.g., in 3T3 cells expressing a wild type EGFR, a mutant EGFR, or a fragment of any thereof).

An EGFR sensitizing mutation comprises without limitation L858R, G719S, G719C, G719A, L861Q, a deletion in exon 19 and/or an insertion in exon 20. A drug-resistant EGFR mutant can have without limitation a drug resistance mutation comprising T790M, T854A, L718Q, $C_{797}$S, or D761Y.

The selectivity between wild-type EGFR and EGFR containing one or more mutations as described herein can also be measured using cellular proliferation assays where cell proliferation is dependent on kinase activity. For example, murine Ba/F3 cells transfected with a suitable version of wild-type EGFR (such as VIII; containing a WT EGFR kinase domain), or Ba/F3 cells transfected with L858R/T790M, Del/T790M/L718Q, L858R/T790M/L718Q, L858R/T790M/$C_{797}$S, Del/T790M/$C_{797}$S, L858R/T790M/I941R, or Exon 19 deletion/T790M can be used. Proliferation assays are performed at a range of inhibitor concentrations (10 μM, 3 μM, 1.1 μM, 330 nM, 110 nM, 33 nM, 11 nM, 3 nM, I nM) and an $EC_{50}$ is calculated.

An alternative method to measure effects on EGFR activity is to assay EGFR phosphorylation. Wild type or mutant (L858R/T790M, Del/T790M, Del/T790M/L718Q, L858R/T790M/$C_{797}$S, Del/T790M/$C_{797}$S, L858R/T790M/I941R, or L858R/T790M/L718Q) EGFR can be transfected into NIH-3T3 cells (which do not normally express endogenous EGFR) and the ability of the inhibitor (using concentrations as above) to inhibit EGFR phosphorylation can be assayed. Cells are exposed to increasing concentrations of inhibitor for 6 hours and stimulated with EGF for 10 minutes. The effects on EGFR phosphorylation are assayed by Western Blotting using phospho-specific (Y1068) EGFR antibodies.

In another aspect, the present disclosure relates to a compound that binds to an allosteric site in EGFR, wherein the compound exhibits greater than 2-fold, 3-fold, 5-fold, 10-fold, 25-fold, 50-fold, 100-fold, or 1000-fold inhibition of EGFR containing one or more mutations as described herein (e.g., L858R/T790M, Del/T790M, Del/T790M/L718Q, L858R/T790M/$C_{797}$S, Del/T790M/$C_{797}$S, L858R/T790M/I941R, or L858R/T790M/L718Q) relative to a wild-type EGFR.

In other embodiments, the disclosure provides a compound that binds to an allosteric site in EGFR in combination with a second active agent , wherein said second active agent prevents EGFR dimer formation, wherein the compound in combination with the second active agent greater than 2-fold, 3-fold, 5-fold, 10-fold, 25-fold, 50-fold, 100-fold, or 1000-fold inhibition of EGFR containing one or more mutations as described herein (e.g., L858R/T790M, Del/T790M, Del/T790M/L718Q, Del/T790M/$C_{797}$S, L858R/T790M/$C_{797}$S, L858R/T790M/I941R, or L858R/T790M/L718Q) relative to a wild-type EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In still another aspect, the disclosure provides a method of inhibiting epidermal growth factor receptor (EGFR), the method comprising administering to a subject in need thereof an effective amount of a compound of disclosed herein, or a pharmaceutically acceptable salt thereof. In some embodiments, the method further comprises administering a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In another aspect, provided herein is a method of treating or preventing a disease, the method comprising administering to a subject in need thereof an effective amount of a compound of disclosed herein, or a pharmaceutically acceptable salt thereof. In some embodiments, the disease is mediated by a kinase. In further embodiments, the kinase comprises a mutated cysteine residue. In further embodiments, the mutated cysteine residue is located in or near the position equivalent to Cys 797 in EGFR, including such positions in Jak3, Blk, Bmx, Btk, HER2 (ErbB2), HER4 (ErbB4), Itk, Tec, and Txk. In some embodiments, the method further comprises administering a second active agent, wherein said second active agent prevents dimer formation of the kinase. In some embodiments, the second active agent that prevents kinase dimer formation is an antibody. In further embodiments, the second active agent prevents EGFR dimer formation. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

In some embodiments, the disease is mediated by EGFR (e.g., EGFR plays a role in the initiation or development of the disease). In some embodiments, the disease is mediated by a Her-kinase. In further embodiments, the Her-kinase is HER1, HER2, or HER4.

In certain embodiments, the disease is resistant to a known EGFR inhibitor, including but not limited to, gefitinib, erlotinib, osimertinib, CO-1686, or WZ4002. In certain embodiments, a diagnostic test is performed to determine if the disease is associated with an activating mutation in EGFR. In certain embodiments, a diagnostic test is performed to determine if the disease is associated with an EGFR harboring an activating mutation and/or a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, $C_{797}$S, or D761Y. The diagnostic test can comprise sequencing, pyrosequencing, PCR, RT-PCR, or similar analysis techniques known to those of skill in the art that can detect nucleotide sequences.

In certain embodiments, the disease is cancer or a proliferation disease.

In further embodiments, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the disease is lung cancer, breast cancer, glioma, squamous cell carcinoma, or prostate cancer. In still further embodiments, the disease is non-small cell lung cancer.

In certain embodiments, the disease is resistant to a known EGFR inhibitor, including but not limited to, gefitinib, erlotinib, osimertinib, CO-1686, or WZ4002. In certain embodiments, a diagnostic test is performed to determine if the disease is associated with an activating mutation in EGFR. In certain embodiments, a diagnostic test is performed to determine if the disease is associated with an EGFR harboring an activating mutation and/or a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, $C_{797}S$, or D761Y. The diagnostic test can comprise sequencing, pyrosequencing, PCR, RT-PCR, or similar analysis techniques known to those of skill in the art that can detect nucleotide sequences.

In yet another aspect, provided herein is a method of treating a kinase-mediated disorder comprising administering to a subject in need thereof an effective amount of a compound disclosed herein, or a pharmaceutically acceptable salt thereof. In some embodiments, the compound is an inhibitor of HER1, HER2, or HER4. In other embodiments, the subject is administered an additional therapeutic agent. In other embodiments, the compound and the additional therapeutic agent are administered simultaneously or sequentially.

In another aspect, the disclosure provides a method of treating a kinase mediated disorder, the method comprising administering to a subject in need thereof an effective amount of a compound of disclosed herein, or a pharmaceutically acceptable salt thereof, and a second active agent, wherein said second active agent prevents EGFR dimer formation. In some embodiments, the compound is an inhibitor of HER1, HER2, or HER4. In other embodiments, the subject is administered an additional therapeutic agent. In other embodiments, the compound, the second active agent that prevents EGFR dimer formation, and the additional therapeutic agent are administered simultaneously or sequentially. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. in an embodiment, the second active agent is an ATP competitive EGFR inhibitor. In another embodiment, the ATP competitive EGFR inhibitor is osimertinib, gefitinib or erlotinib. in another embodiment, the ATP competitive EGFR inhibitor is osimertinib.

In other embodiments, the disease is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the disease is lung cancer, breast cancer, glioma, squamous cell carcinoma, or prostate cancer. In still further embodiments, the disease is non-small cell lung cancer.

In another aspect, provided herein is a method of treating cancer, wherein the cancer cell comprises activated EGFR, comprising administering to a subject in need thereof an effective amount of a compound of disclosed herein, or a pharmaceutically acceptable salt thereof.

In another aspect, provided herein is a method of treating cancer, wherein the cancer cell comprises activated EGFR, comprising administering to a subject in need thereof an effective amount of a compound of disclosed herein, or a pharmaceutically acceptable salt thereof and a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. in an embodiment, the second active agent is an ATP competitive EGFR inhibitor, In another embodiment, the ATP competitive EGFR inhibitor is osimertinib, gefitinib or erlotinib. in another embodiment, the ATP competitive EGFR inhibitor is osimertinib, In certain embodiments, the EGFR activation is selected from mutation of EGFR, amplification of EGFR, expression of EGFR, and ligand mediated activation of EGFR.

In further embodiments, the mutation of EGFR is selected from G719S, G719C, G719A, L858R, L861Q, an exon 19 deletion mutation, and an exon 20 insertion mutation.

In still another aspect, provided herein is a method of treating cancer in a subject, wherein the subject is identified as being in need of EGFR inhibition for the treatment of cancer, comprising administering to the subject an effective amount of a compound disclosed herein, or a pharmaceutically acceptable salt thereof.

In certain embodiments, the subject identified as being in need of EGFR inhibition is resistant to a known EGFR inhibitor, including but not limited to, gefitinib, erlotinib, osimertinib, CO-1686, or WZ4002. In certain embodiments, a diagnostic test is performed to determine if the subject has an activating mutation in EGFR. In certain embodiments, a diagnostic test is performed to determine if the subject has an EGFR harboring an activating mutation and/or a drug resistance mutation. Activating mutations comprise without limitation L858R, G719S, G719C, G719A, L718Q, L861Q, a deletion in exon 19 and/or an insertion in exon 20. Drug resistant EGFR mutants can have without limitation a drug resistance mutation comprising T790M, T854A, L718Q, $C_{797}S$, or D761Y. The diagnostic test can comprise sequencing, pyrosequencing, PCR, RT-PCR, or similar analysis techniques known to those of skill in the art that can detect nucleotide sequences.

In an aspect, provided herein is a method of preventing resistance to a known EGFR inhibitor (including but not limited to gefitinib, erlotinib, osimertinib, CO-1686, or WZ4002) in a subject, comprising administering to a subject in need thereof an effective amount of a compound disclosed herein, or a pharmaceutically acceptable salt thereof.

In another aspect, provided herein is a method of preventing resistance to a known EGFR inhibitor (including but not limited to gefitinib, erlotinib, osimertinib, CO-1686, or WZ4002) in a disease, comprising administering to a subject in need thereof an effective amount of a compound disclosed herein, or a pharmaceutically acceptable salt thereof, and a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab.

In an embodiment of the methods disclosed herein, the subject is a human.

In another aspect, the disclosure provides a compound disclosed herein, or a pharmaceutically acceptable salt thereof, for use in the manufacture of a medicament for treating or preventing a disease in which EGFR plays a role.

In an aspect, provided herein is a method of treating or preventing a condition selected from the group consisting of autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease. In other embodiments, said condition is selected from a proliferative disorder and a neurodegenerative disorder.

One aspect of this disclosure provides compounds that are useful for the treatment of diseases, disorders, and conditions characterized by excessive or abnormal cell proliferation. Such diseases include, but are not limited to, a proliferative or hyperproliferative disease, and a neurodegenerative disease. Examples of proliferative and hyperproliferative diseases include, without limitation, cancer. The term "cancer" includes, but is not limited to, the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, colorectal, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon, rectum, large intestine, rectum, brain and central nervous system, chronic myeloid leukemia (CML), and leukemia. The term "cancer" includes, but is not limited to, the following cancers: myeloma, lymphoma, or a cancer selected from gastric, renal, head and neck, oropharangeal, non-small cell lung cancer (NSCLC), endometrial, hepatocarcinoma, non-Hodgkin's lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodysplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the disclosure, the present disclosure provides for the use of one or more compounds of the disclosure in the manufacture of a medicament for the treatment of cancer, including without limitation the various types of cancer disclosed herein.

In some embodiments, the compounds of this disclosure are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease. In some embodiments, the compounds of this disclosure are useful for treating hematopoietic disorders, in particular, acute-myelogenous leukemia (AML), chronic-myelogenous leukemia (CML), acute-promyelocytic leukemia, and acute lymphocytic leukemia (ALL).

The term "cancerous cell" as provided herein, includes a cell afflicted by any one of the above-identified conditions.

The disclosure further provides a method for the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias, or pre-cancerous lesions from continuing to expand or from becoming cancerous. Examples of pre-cancerous lesions may occur in skin, esophageal tissue, breast and cervical intra-epithelial tissue.

Examples of neurodegenerative diseases include, without limitation, adrenoleukodystrophy (ALD), Alexander's disease, Alper's disease, Alzheimer's disease, amyotrophic lateral sclerosis (Lou Gehrig's Disease), ataxia telangiectasia, Batten disease (also known as Spielmeyer-Vogt-Sjogren-Batten disease), bovine spongiform encephalopathy (BSE), Canavan disease, Cockayne syndrome, corticobasal degeneration, Creutzfeldt-Jakob disease, familial fatal insomnia, frontotemporal lobar degeneration, Huntington's disease, HIV-associated dementia, Kennedys disease, Krabbe's disease, Lewy body dementia, neuroborreliosis, Machado-Joseph disease (spinocerebellar ataxia type 3), multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Batten disease (also known as Batten disease), spinocerebellar ataxia (multiple types with varying characteristics), spinal muscular atrophy, Steele-Richardson-Olszewski disease, tabes dorsalis, and toxic encephalopathy.

Another aspect of this disclosure provides a method for the treatment or lessening the severity of a disease selected from a proliferative or hyperproliferative disease, or a neurodegenerative disease, comprising administering an effective amount of a compound, or a pharmaceutically acceptable composition comprising a compound, to a subject in need thereof. In other embodiments, the method further comprises administering a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. In an embodiment, the second active agent is an ATP competitive EGFR inhibitor. In another embodiment, the ATP competitive EGFR inhibitor is osimertinib, gefitinib or erlotinib. In another embodiment, the ATP competitive EGFR inhibitor is osimertinib.

The activity of the compounds and compositions of the present disclosure as EGFR kinase inhibitors may be assayed in vitro, in vivo, or in a cell line. In vitro assays include assays that determine inhibition of either the kinase activity or ATPase activity of the activated kinase. Alternate in vitro assays quantitate the ability of the inhibitor to bind to the protein kinase and may be measured either by radio labelling the inhibitor prior to binding, isolating the inhibitor/kinase complex and determining the amount of radio label bound, or by running a competition experiment where new inhibitors are incubated with the kinase bound to known radioligands. Detailed conditions for assaying a compound utilized in this disclosure as an inhibitor of various kinases are set forth in the Examples below.

In accordance with the foregoing, the present disclosure further provides a method for preventing or treating any of the diseases or disorders described above in a subject in need of such treatment, which method comprises administering to said subject a therapeutically effective amount of a compound of the disclosure, or a pharmaceutically acceptable salt thereof, and optionally a second active agent, wherein said second active agent prevents EGFR dimer formation. For any of the above uses, the required dosage will vary depending on the mode of administration, the particular condition to be treated and the effect desired.

In other embodiments, the compound and the second active agent that prevents EGFR dimer formation are administered simultaneously or sequentially.

Administration/Dosages/Formulations

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, com, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations (for example, sterile injectable aqueous or oleaginous suspensions) may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this disclosure with suitable non-irritating excipients or carriers such as cocoa butter, polyethylene glycol, or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this disclosure.

The ointments, pastes, creams and gels may contain, in addition to an active compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this disclosure, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present disclosure, disorders are treated or prevented in a subject, such as a human or other animal, by administering to the subject a therapeutically effective amount of a compound of the disclosure, in such amounts and for such time as is necessary to achieve the desired result. The term "therapeutically effective amount" of a compound of the disclosure, as used herein, means a sufficient amount of the compound so as to decrease the symptoms of a disorder in a subject. As is well understood in the medical arts a therapeutically effective amount of a compound of this disclosure will be at a reasonable benefit/risk ratio applicable to any medical treatment.

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g., humans, is in the range from about 0.5 mg to about 100 mg, conveniently administered, e.g., in divided doses up to four times a day or in retard form. Suitable unit dosage forms for oral administration comprise from ca. 1 to 50 mg active ingredient.

In certain embodiments, a therapeutic amount or dose of the compounds of the present disclosure may range from about 0.1 mg/Kg to about 500 mg/Kg, alternatively from about 1 to about 50 mg/Kg. In general, treatment regimens according to the present disclosure comprise administration to a patient in need of such treatment from about 10 mg to about 1000 mg of the compound(s) of this disclosure per day in single or multiple doses. Therapeutic amounts or doses will also vary depending on route of administration, as well as the possibility of co-usage with other agents.

Upon improvement of a subject's condition, a maintenance dose of a compound, composition or combination of this disclosure may be administered, if necessary. Subsequently, the dosage or frequency of administration, or both, may be reduced, as a function of the symptoms, to a level at which the improved condition is retained; when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present disclosure will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The disclosure also provides for a pharmaceutical combination, e.g., a kit, comprising a) a first agent which is a compound of the disclosure as disclosed herein, in free form or in pharmaceutically acceptable salt form, and b) at least one co-agent. The kit can comprise instructions for its administration.

In certain embodiments, these compositions optionally further comprise one or more additional therapeutic agents. For example, an agent that prevents EGFR dimer formation, chemotherapeutic agents or other antiproliferative agents may be combined with the compounds of this disclosure to treat proliferative diseases and cancer.

Some examples of materials which can serve as pharmaceutically acceptable carriers include, but are not limited to, ion exchangers; alumina; aluminum stearate; lecithin; serum proteins, such as human serum albumin; buffer substances such as phosphates, glycine, sorbic acid, or potassium sorbate; partial glyceride mixtures of saturated vegetable fatty acids; water; salts or electrolytes, such as protamine sulfate; disodium hydrogen phosphate; potassium hydrogen phosphate; sodium chloride; zinc salts; colloidal silica; magnesium trisilicate; polyvinyl pyrrolidone; polyacrylates; waxes; polyethylenepolyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such a propylene glycol or polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions. Further, non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present disclosure.

Kits

In an aspect, provided herein is a kit comprising a compound capable of inhibiting kinase activity selected from one or more compounds of disclosed herein, or pharmaceutically acceptable salts thereof, and instructions for use in treating cancer. In certain embodiments, the kit further comprises components for performing a test to determine whether a subject has activating and/or drug resistance mutations in EGFR.

In another aspect, the disclosure provides a kit comprising a compound capable of inhibiting EGFR activity selected from a compound disclosed herein, or a pharmaceutically acceptable salt thereof.

In another aspect, the disclosure provides a kit comprising a compound capable of inhibiting kinase activity selected from one or more compounds of disclosed herein, or pharmaceutically acceptable salts thereof; a second active agent, wherein said second active agent prevents EGFR dimer formation; and instructions for use in treating cancer. In certain embodiments, the kit further comprises components for performing a test to determine whether a subject has activating and/or drug resistance mutations in EGFR. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab.

In another aspect, the disclosure provides a kit comprising a compound capable of inhibiting EGFR activity selected from a compound of disclosed herein, or a pharmaceutically acceptable salt thereof and a second active agent, wherein said second active agent prevents EGFR dimer formation. In some embodiments, the second active agent that prevents EGFR dimer formation is an antibody. In further embodiments, the second active agent that prevents EGFR dimer formation is cetuximab, trastuzumab, or panitumumab. In further embodiments, the second active agent that prevents EGFR dimer formation is cetuximab. in an embodiment, the second active agent is an ATP competitive EGFR inhibitor, In another embodiment, the ATP competitive EGFR inhibitor is osimertinib, gefitinib or erlotinib. in another embodiment ; the ATP competitive EGFR inhibitor is osimertinib.

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

The application is further illustrated by the following examples, which should not be construed as further limiting. The practice of the present disclosure will employ, unless otherwise indicated, conventional techniques of organic synthesis, cell biology, cell culture, and molecular biology, which are within the skill of the art.

Abbreviations

AcOH acetic acid

DBU 1,8-diazabicyclo[5.4.0]undec-7-ene

DCM dichloromethane

DIAD diisopropyl azodicarboxylate

DIEA diisopropylethylamine

DMA dimethylacetamide

DMF dimethylformamide

DMSO dimethylsulfoxide

DPPA diphenylphosphoryl azide dppf 1,1'-bis(diphenylphosphino)ferrocene

EtOAc/EA ethyl acetate

EtOH ethanol

HATU (1-[bis(dimethylamino)methylene]-1H-1,2,3-triazolo[4,5-b]pyridinium 3-oxide hexafluorophosphate MeCN/ACN acetonitrile MeOH methanol NMP N-methyl-2-pyrrolidone pet.ether/PE petroleum ether $PPh_3$ triphenylphosphine rt room temperature SEM (trimethylsilyl)ethoxymethyl TEA triethylamine THF tetrahydrofuran TMS trimethylsilyl

Synthetic Procedures

Example 1

Scheme 1. Preparation of Intermediate 0216-8

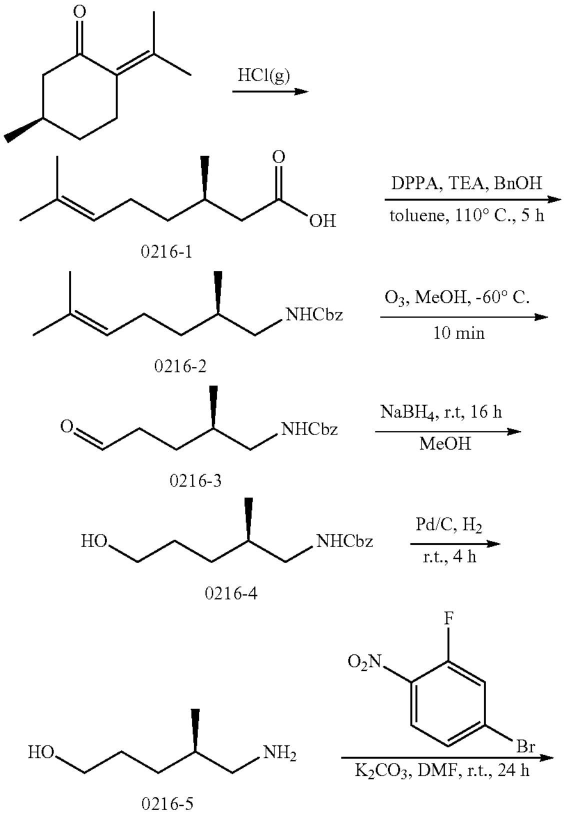

0216-1

0216-2

0216-3

0216-4

0216-5

-continued

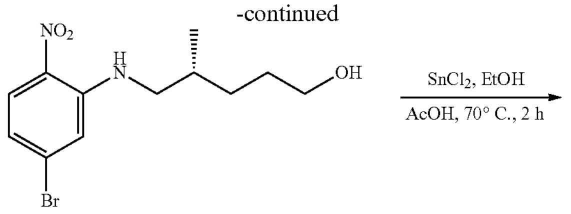

0216-6

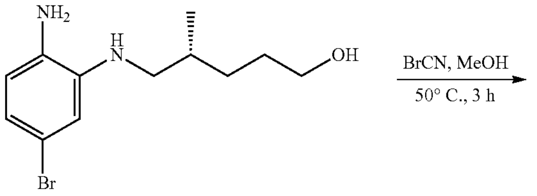

0216-7

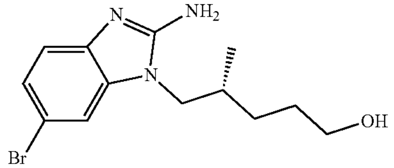

0216-8

Step 1

To a 250 ml three-necked flask, pulegone (40.0 g, 263.0 mmol) was added and cooled to 0° C. with stirring. HCl (g, 16.0 g, 428.0 mmol) was bubbled to the reaction. The mixture was transfered to a 100 mL sealed tube and warmed to r.t. with stirring overnight. The reaction mixture was poured into aqueous KOH (5% Wt, 800 mL) and stirred for 3 h at r.t. The mixture was extracted with EtOAc and organic phase was discarded. The aqueous phase was acidified to pH=1 with conc. HCl and extracted with EtOAc (500 mL×3). The combined organic phase was dried over $Na_2SO_4$, concentrated under reduce pressure to afford compound 0216-1 (25 g, yield 55.9%) as colorless oil. $^1$H NMR (400 MHz, Chloroform-d) d) δ 5.09 (tt, J=7.1, 1.5 Hz, 1H), 2.36 (dd, J=15.0, 5.8 Hz, 1H), 2.15 (dd, J=14.9, 8.2 Hz, 1H), 2.10-1.87 (m, 3H), 1.68 (d, J=1.6 Hz, 3H), 1.60 (d, J=1.3 Hz, 3H), 1.38 (ddt, J=12.6, 9.3, 6.2 Hz, 1H), 1.24 (dddd, J=13.6, 9.1, 7.7, 6.2 Hz, 1H), 0.98 (d, J=6.6 Hz, 3H).

Step 2

A solution of (R)-3,7-dimethyloct-6-enoic acid (5.0 g, 29.4 mmol) and TEA (3.26 g, 32.3 mmol) in 30 mL of toluene was stirred at 80° C. for 1 hour. DPPA (8.9 g, 32.3 mmol) was dropwised, then the reaction was warmed at 110° C. and stirred for 4 hours. After cooling, the mixture was poured into water (300 mL) and extracted with EtOAc (50 mL×3), washed with water (200 mL×2) and brine (200 mL×2), dried with $Na_2SO_4$. The solvent was removed under reduced pressure then the residue was purified by column chromatography eluted with ethyl acetate/pet.ether=40/1 to afford the compound 0216-2 (3 g, 37.1%). $^1$H NMR (400 MHz, Chloroform-c) δ7.51-7.27 (m, 5H), 5.08 (d, J=9.9 Hz, 3H), 4.76 (s, 1H), 3.14 (dt, J=12.6, 6.1 Hz, 1H), 3.02 (dt, J=13.3, 6.6 Hz, 1H), 2.15-1.86 (m, 2H), 1.68 (d, J=1.6 Hz, 3H), 1.61 (s, 1H), 1.60 (s, 3H), 1.37 (ddt, J=11.9, 9.2, 5.9 Hz, 1H), 1.14 (dtd, J=14.0, 8.6, 5.8 Hz, 1H), 0.90 (d, J=6.7 Hz, 3H).

Step 3

0216-2 (5.0 g, 18.2 mmol) dissovled in 100 mL methanol, the solution was cooled to −60° C., ozone was bubbled through the solution until a dark blue color persisted. The reaction was quenched with dimethyl sulfide. The reaction was concentrated to furnish the aldehyde 0216-3 as an oil.

Step 4

0216-2 (4.5 g, 18 mmol), DBU (4.1 g, 27.2 mmol), and NaBH 4 (4.1 g, 109.0 mmol) dissoved in 90 mL methanol, stirred at 0° C. for 30 min, left the reaction at r.t. overnight. The mixture was poured into water (100 mL), methanol was evaporated, the mixture was extracted with EtOAc (20 mL×3), washed with water (30 mL×2) and brine (30 mL×2), dried with $Na_2SO_4$. The solvent was removed under reduced pressure then the residue was purified by column chromatography eluted with EA/PE=7:1 to afford the compound 0216-4 (2.5 g, 55%). $^1$H NMR (400 MHz, Chloroform-d) δ 7.42-7.27 (m, 5H), 5.09 (s, 2H), 4.86 (s, 1H), 3.62 (t, J=6.4 Hz, 2H), 3.14 (dt, J=12.7, 6.2 Hz, 1H), 3.03 (dt, J=13.4, 6.5 Hz, 1H), 1.65 (dq, J=11.6, 5.9 Hz, 4H), 1.43 (ddd, J=13.1, 10.7, 5.4 Hz, 1H), 1.24-1.11 (m, 1H), 0.91 (d, J=6.7 Hz, 3H).

Step 5

0216-4 (370 mg, 1.5 mmol) and 190 mg Pd/C (10%) in 5 mL methanol, air was changed by hydrogen three time, stirred at r.t. 4 h, filtered Pd/C, methanol was evaporated to afford 0216-5 (150 mg, 87.0%). $^1$H NMR (400 MHz, DMSO-d 6) 6 8.02 (s, 3H), 3.56 (s, 1H), 3.37 (t, J=6.2 Hz, 1H), 2.71 (dt, J=12.0, 5.9 Hz, 1H), 2.62-2.51 (m, 1H), 1.73 (ddt, J=12.5, 7.5, 3.8 Hz,1H), 1.52-1.27 (m, 3H), 1.20-1.02 (m, 1H), 0.91 (d, J=6.7 Hz, 3H).

Step 6

A mixture of 4-bromo-2-fluoro-1-nitrobenzene (1.86 g, 8.45 mmol), 0216-5 (0.9 g, 7.68 mmol) and $K_2CO_3$ (2.34 g, 16.9 mmol) in DMF (20 mL) stirred at r.t. for 24 h. The mixture was poured into water (200 mL), extracted with EtOAc (20 mL×3), washed with water (30 mL×2) and brine (30 mL×2), dried with $Na_2SO_4$. The solvent was removed under reduced pressure then the residue was purified by column chromatography eluted with ethyl acetate/pet.ether=6/1 to afford the compound 0216-6 (1.8 g, 73.9%). $^1$H NMR (400 MHz, DMSO-$d_6$) δ 8.19 (t, J=5.6 Hz, 1H), 7.98 (d, J=9.1 Hz, 1H), 7.25 (d, J=2.0 Hz, 1H), 6.82 (dd, J=9.1, 2.0 Hz, 1H), 4.38 (t, J=5.1 Hz, 1H), 3.39 (q, J=5.9 Hz, 2H), 3.30-3.24 (m, 1H), 3.17 (ddd, J=13.1, 7.3, 5.6 Hz, 1H), 1.89-1.73 (m, 1H), 1.57-1.35 (m, 3H), 1.28-1.13 (m, 1H), 0.94 (d, J=6.6 Hz, 3H).

Step 7

A mixture of 0216-6 (278 mg, 0.91 mmol) and $SnCl_2$ (1021 mg, 4.52 mmol) in AcOH (0.5 mL) and EtOH (5 mL) was stirred at 70° C. for 2 hours. After cooling, the mixture was added $Na_2CO_3$ (480 mg, 4.52 mmol) and stirred for 1 hour at r.t., then added KF (1.05 g, 18.1 mmol) and stirred for 4 hours at r.t. The mixture was filtered and the residue was concentrated. The crude was dissolved into EtOAc (10 ml), washed with water (5 mL×2) and brine (5 mL), dried with $Na_2SO_4$. The solvent was removed under reduced pressure then the residue was purified by column chromatography eluted with ethyl acetate/pet.ether=3/1 to afford the compound 0216-6 (150 mg, 57.7%). ESI-MS (El+, m/z): 288.95.

Step 8

A mixture of 0216-7 (7.9 g, 27.6 mmol) and BrCN (4.4 g, 41.5 mmol) in MeOH (80 mL) was stirred at 50° C. for 3 h. After cooling, the mixture was concentrated and the crude was purified by column chromatography eluted with DCM/MeOH=30/1 to afford the compound 0216-8 (8.0 g, 92.8%). ESI-MS (El+, m/z): 313.95.

Scheme 2. Preparation of Intermediate 0216-12

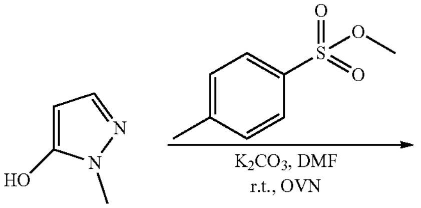

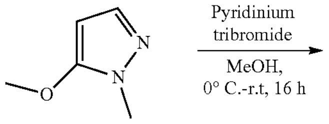

0216-9

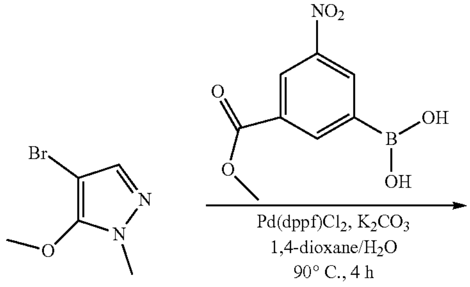

0216-10

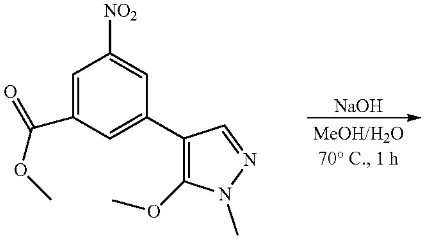

0216-11

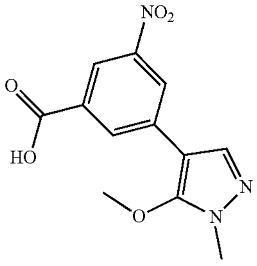

0216-12

Step 1

A mixture of 1-methyl-1H-pyrazol-5-ol (5 g, 51.0 mmol), methyl 4-methylbenzenesulfonate (28.5 g, 152.9 mmol) and $K_2CO_3$ (28.1 g, 203.9 mmol) in DMF (75 mL) was stirred at r.t. over night. The mixture was poured into water (1 L), added conc. HCl to tune pH=3, extracted with EtOAc (300 mL), washed with water (30 mL×2) and brine (30 mL×2), dried with $Na_2SO_4$. The solvent was removed under reduced pressure without further purification to get 1.2g 0216-9 (12%). $^1H$ NMR (400 MHz, DMSO-$d_6$) δ 7.20 (d, J=2.0 Hz, 1H), 5.62 (d, J=2.0 Hz, 1H), 3.83 (s, 3H), 3.52 (s, 3H).

Step 2

0216-9 (10.1 g, 90.2 mmol) was dissoved in 200 mL methanol, stirred at 0° C., pyridinium tribromide (28.8g, 90.2 mmol) was added, after 10 min, removed the cold bath and left the mixture at r.t. overnight. The mixture was poured into water (1000 mL), the mixture was extracted with EtOAc (200 mL×3), washed with water (200 mL×2) and brine (100 mL×2), dried with $Na_2SO_4$. The solvent was removed under reduced pressure to afford the compound 0216-10 (11 g, 64%). ESI-MS (El+, m/z): 193.05

Step 3

A mixture of 0216-10 (9.1 g, 47.7 mmol), (3-(methoxycarbonyl)-5-nitrophenyl)boronic acid (12.9 g, 57.2 mmol), Pd(dppf)$Cl_2$ (3.5 g, 4.8 mmol) and $K_2CO_3$ (13.2 g, 95.4 mmol) in dioxane (225 mL) and water (45 mL) was stirred at 90° C. under $N_2$ protection for 4 h. After cooling, the mixture was filtered and the residue was poured into water (1 L), extracted with EtOAc (200 mL×3), washed with brine (300 mL), dried with $Na_2SO_4$. The solvent was removed under reduced pressure then the residue was purified by column chromatography eluted with ethyl acetate/pet.ether=5/1 to afford the compound 0216-11 (2.2 g, 16.8%). ESI-MS (El+, m/z): 292.15.

Step 4

To a solution of compound 0216-11 (2.5 g, 8.5 mmol) in methanol (30 mL)/water (15 mL) was added NaOH (1.0 g, 25.5 mmol). The reaction was stirred for 1 h at 70° C. The reaction was diluted with water (20 mL), concentrated under reduce pressure to ⅗ column. The mixture was acidified to pH=3 with 4N HCl aqueous in water. The precipitate was collected by filtration and dried to afford compound 0216-12 (2.0 g, yield 84.9%) as off-white solid. ESI-MS (El+, m/z): 278.15.

Scheme 3 Preparation of Compound 001

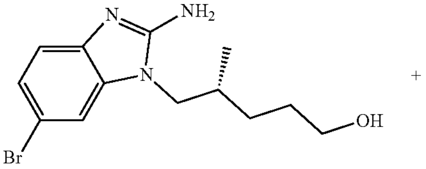

0216-8

-continued

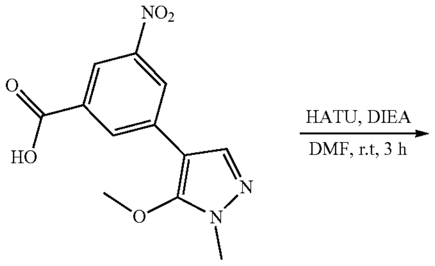

0216-12

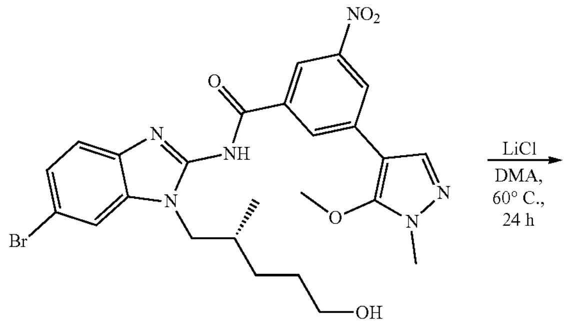

0216-13

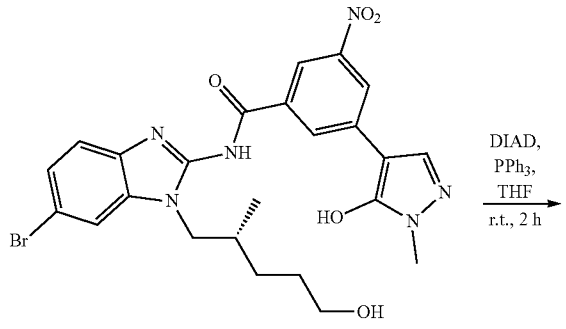

0216-14

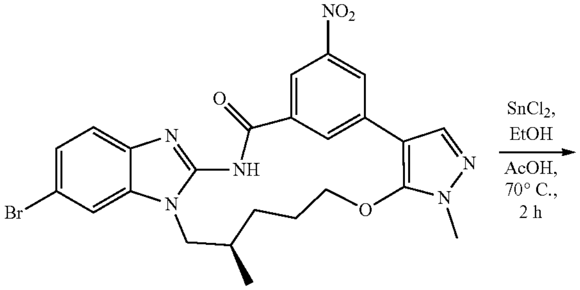

0216-15

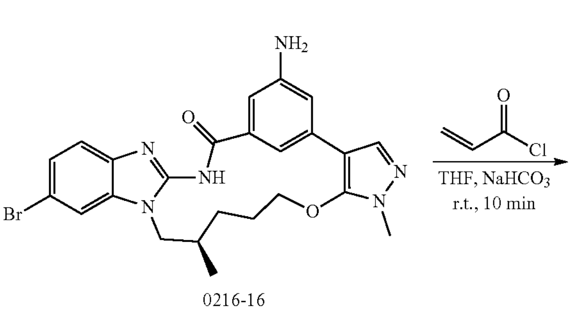

0216-16

-continued

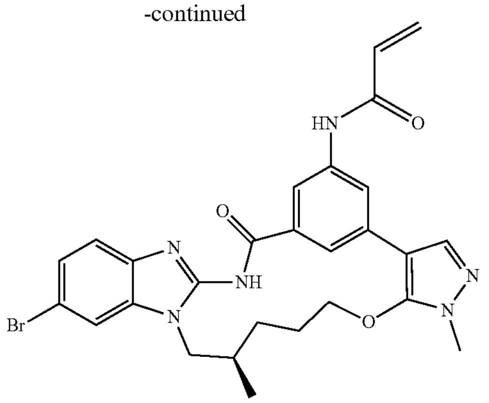

001

Step 1

To a solution of compound 0216-11 (1.0 g, 3.6 mmol) and 0216-8 (0.9 g, 3.0 mmol) in DMF (20 mL) at r.t. was added HATU (1.7 g, 4.5 mmol) and DIEA (1.2 g, 9.0 mmol). The reaction was stirred for 3 h at r.t. The reaction was poured into water (200 mL) and extracted with EtOAc (30 mL×3), washed with brine (50 mL×3), dried with $Na_2SO_4$. The solvent was removed under reduced pressure then the residue was purified by prep-HPLC to afford 0216-13 (0.35 g, 17.0%) as a yellow solid. ESI-MS (EI+, m/z): 571.43.

Step 2

To a solution of compound 0216-13 (610 mg, 1.1 mmol) and LiCl (905 mg, 21.4 mmol) in DMA (8 mL) was stirred at 60° C. for 24 h. The reaction was cooled to r.t., diluted with water (50 mL). The black precipitate was collected by centrifugation, dissolved in methanol/DCM (30 mL, v/v=1/5). The solvent was dried over Na2SO4, concentrated under reduce pressure. The crude product was purified through SGC (methanol/DCM=1/20) to afford compound 0216-14 (300 mg, yield 50.8%) as yellow solid. ESI-MS (EI+, m/z): 557.41.

Step 3

$PPh_3$ (188 mg, 0.72 mmol) was dissovled in 1 mL dry THF, DIAD (145 mg, 0.72 mmol) was added, 0216-14 (80 mg, 0.14 mmol) dissovled in 1 mL THF and dropped in the mixture, reacted at r.t. for 2 h, the mixture purified by HPLC to get 0216-15 (60 mg, 77%). ESI-MS (EI+, m/z): 539.20.

Step 4

To a solution of compound 0216-15 (135 mg, 0.25 mmol) at r.t. in ethanol (5 mL) was added $SnCl_2 \cdot H_2O$ (282 mg, 1.25 umol). The reaction was heated at 70° C. for 2 h. The reaction was quenched with saturated $NaHCO_3$ (20 mL) aqueous in water, extracted with EtOAc (20 mL×5). The combined organic phase was dried over $Na_2SO_4$, concentrated under reduce pressure. The crude product was purified through SGC (methanol/DCM=1/10) to afford 0216-16 (70 mg, yield 55%) as yellow solid. ESI-MS (EI+, m/z): 509.30.

Step 5

To a solution of 0216-16 (64 mg, 0.126 mmol) in THF (3 mL)/std aqueous $NaHCO_3$ (0.6 mL) at 0° C. was added dropwise acryloyl chloride (1 M in DCM, 251 uL). The reaction was warmed to r.t. and stirred for 15 min. The reaction was purified by prep-HPLC directly to afford compound 001 (40 mg, yield 56.4%) as yellow solid. ESI-MS (El+, m/z): 563.25. $^1$H NMR (400 MHz, DMSO-$d_6$) δ 12.75 (s, 1H), 10.29 (s, 1H), 8.51 (d, J=1.7 Hz, 1H), 8.15-8.07 (m, 2H), 7.88 (d, J=1.8 Hz, 1H), 7.69 (s, 1H), 7.45 (d, J=8.4 Hz, 1H), 7.36 (dd, J=8.4, 1.7 Hz, 1H), 6.47 (dd, J=16.9, 10.1 Hz, 1H), 6.29 (dd, J=17.0, 2.0 Hz, 1H), 5.78 (dd, J=10.1, 2.0 Hz, 1H), 4.35 (s, 1H), 4.16 (s, 2H), 4.03-3.90 (m, 2H), 3.72 (s, 3H), 3.17 (d, J=4.6 Hz, 1H), 2.80 (s, 1H), 2.16 (d, J=17.2 Hz, 1H), 1.91 (d, J=9.8 Hz, 2H), 1.43 (q, J=10.0 Hz, 1H), 0.81 (d, J=6.5 Hz, 3H).

Example 2

Scheme 4. Preparation of Compound 002

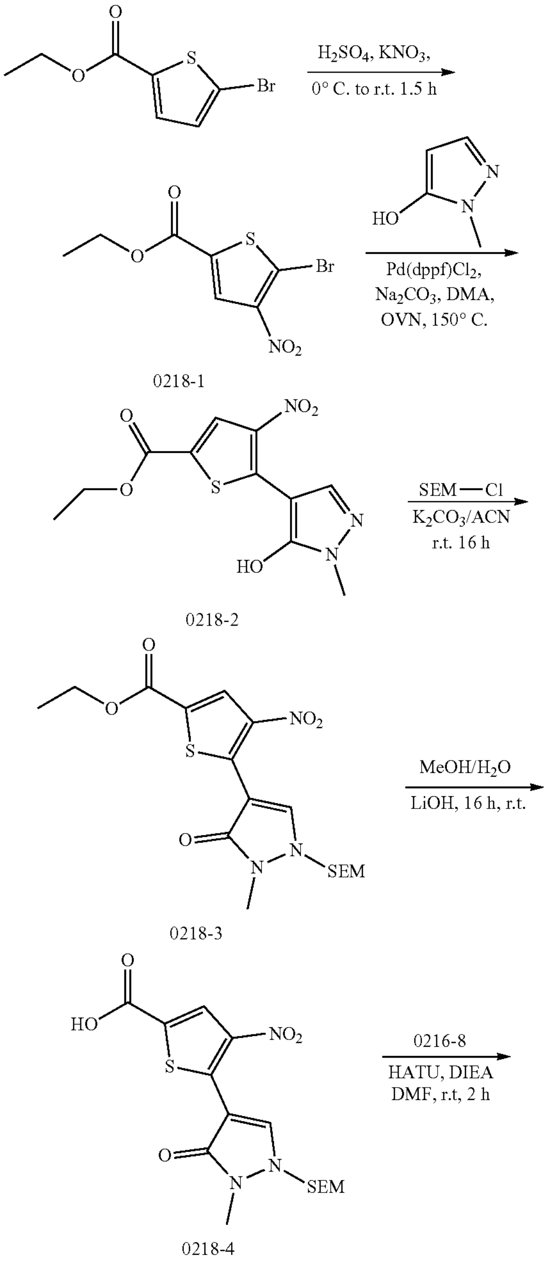

0218-1

0218-2

0218-3

0218-4

-continued

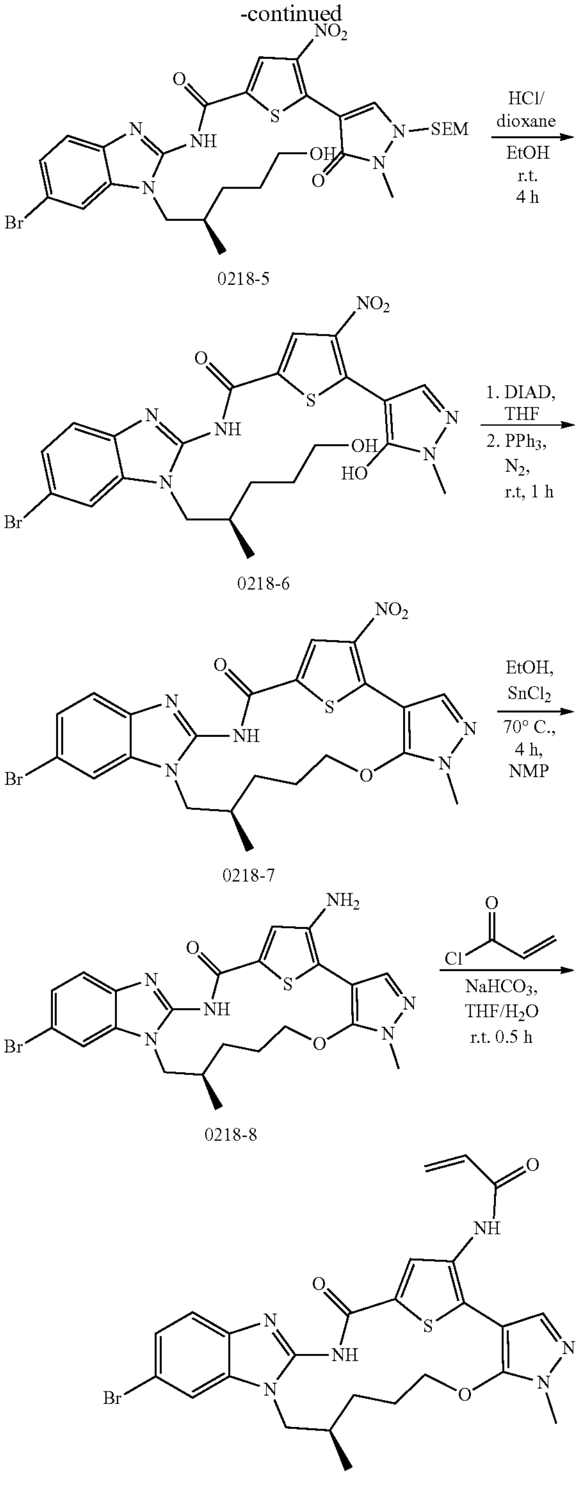

0218-5

0218-6

0218-7

0218-8

002

Step 1

A solution of ethyl 5-bromothiophene-2-carboxylate (1 g, 42.0 mmol), $KNO_3$ (518 mg, 51.2 mmol) in $H_2SO_4$ (10 mL) was stirred at r.t. for 4 h. TLC showed the reaction was completed. The reaction was diluted with $H_2O$, adjusted pH to 7, and extracted with ethyl acetate. The solvent was removed under reduced pressure then the residue was purified by column chromatography (Petroleum ether:EtOAc, 20:1) to afford the compound 0218-1 (700 mg, 58.3%). ESI-MS ($EI^+$, m/z): 282.40.

Step 2

To a solution of 0218-1 (100 mg, 0.358 mmol) in DMA (3 mL) at rt was added 1-methyl-1H-pyrazol-5-ol (35.13 mg,0.358 mmol), Pd(dppf)$Cl_2$ (289.35 mg, 0.035 mmol), and $Na_2CO_3$ (196.70 mg,0.716 mmol). The mixture was stirred at 150° C. for 3 h. The mixture was filtered and washed with EtOAc (20 mL×3). The combined organic layers were dried over $Na_2SO_4$ and concentrated under reduced pressure. The residue was purified by RP-column chromatography to afford 0218-2 (80 mg, 50%). ESI-MS(EI[30] , m/z): 298.06.

Step 3

To a solution of 0218-2 (100 mg, 0.3365 mmol) in MeCN (3 mL) at rt was added $K_2CO_3$ (93.05 mg,0.6733 mmol) and SEM-CI (84.19 mg, 0.5049 mmol). The mixture was stirred at rt for 16 h. The mixture was filtered and extracted with EtOAc (20 mL×3). The combined organic layers were washed with water (20 mL), dried over $Na_2SO_4$, and concentrated under reduced pressure. The residue was purified by SGC (PE:EtOAc=5:1, v/v) to afford 0218-3 (80 mg, 31.01%). ESI-MS($EI^+$, m/z): 428.16.

Step 4

To a solution of 0218-3 (100 mg, 0.2341 mmol) in MeOH/$H_2O$ (3 mL/1 mL) at rt was added LiOH (22.43 mg, 0.4682 mmol) and the mixture was stirred at rt for 16 h. The mixture was concentrated, adjusted pH to 4-5 then extracted with EtOAc (20 mL×3) and the combined organic layers were washed with water (20 mL), dried over $Na_2SO_4$ and concentrated under reduced pressure to afford 0218-4 (80 mg, 31.01%). ESI-MS($EI^+$, m/z): 400.00.

Step 5

To a solution of 0218-4 (100 mg, 0.2505 mmol) in DMF (3 mL) at rt was added (R)-5-(2-amino-6-bromo-1H-benzo[d]imidazol-1-yl)-4-methylpentan-1-ol (78.67 mg, 0.2505 mmol), HATU (142.91 mg, 0.3758 mmol), and DIEA (152.0 mg, 0.7517 mmol). The mixture was then stirred at rt for 3 h. The mixture was diluted with water (20 mL) and extracted with EtOAc (20 mL×3). The combined organic layers were washed with brine (20 mL), dried over $Na_2SO_4$, and concentrated under reduced pressure. The residue was purified by SGC (DCM/MeOH, 100:1, v/v) to afford 0218-5 (80 mg, 31.01%). ESI-MS($EI^+$, m/z): 693.695.

Step 6

To a solution of 0218-5 (500 mg, 0.7223 mmol) in dioxane/EtOH (3 mL/1 mL) at rt was added HCl/dioxane (1 mL). The mixture was stirred at rt for 16 h. The mixture was then concentrated and centrifuged with methanol (5 mL×3). The solid was collected to afford 0218-6 (450 mg, 85%). ESI-MS($EI^+$, m/z): 563.564.

Step 7

To a solution of 0218-6 (10 mg, 0.01779 mmol), DIAD (17.98 mg, 0.08895 mmol) in THF (2 mL) and added $PPh_3$ (23.33 mg, 0.08895 mmol). The mixture was stirred at rt for 1 h under $N_2$. The mixture was then concentrated and purified by Prep-HPLC to afford 0218-7 (20 mg, 85%). ESI-MS($EI^+$, m/z): 545.547.

Step 8

To a solution of 0218-7 (20 mg, 0.0367 mmol) in NMP (3 mL) was added $SnCl_2$ (28 mg, 0.0367 mmol). The mixture was stirred at 70° C. for 4 h. The mixture was then diluted with water (20 mL) and extracted with EtOAc (20 mL×3). The combined organic layers were washed with brine (20 mL), dried over $Na_2SO_4$, and concentrated under reduced pressure. The residue was purified by SGC (DCM/MeOH, 50:1, v/v) to afford 0218-8 (10 mg, 45.1%). ESI-MS($E1^+$, m/z): 515.15.

Step 9

To a solution of 0218-8 (100 mg,) and $NaHCO_3$ (3.0 eq) in THF/$H_2O$ (4 mL/1 mL) at rt was added acryloyl chloride (0.8 eq). The mixture was stirred for 1 h then diluted with water (20 mL) and extracted with EtOAc (30 mL×3). The combined organic layers were dried over $Na_2SO_4$ and concentrated under reduced pressure. The residue was purified by prep-HPLC to afford the 002 (17.1 mg, 49.2%). ESI-MS ($EI^+$, m/z): 569.20. $^1$H NMR (400 MHz, DMSO-$d_6$) δ 12.39 (s, 1H), 9.79 (s, 1H), 7.82 (s, 1H), 7.69 (s, 1H), 7.47 (s, 1H), 7.33 (s, 2H), 6.54 (dd, J=17.1, 10.2 Hz, 1H), 6.26 (dd, J=17.1, 2.0 Hz, 1H), 5.77 (dd, J=10.2, 2.0 Hz, 1H), 4.30 (d, J=9.6 Hz, 1H), 4.07-3.97 (m, 2H), 3.88 (t, J=12.0 Hz, 1H), 3.72 (s, 3H), 2.68 (s, 1H), 2.25-2.08 (m, 2H), 1.87 (d, J=13.7 Hz, 1H), 1.23 (s, 1H), 0.78 (d, J=6.5 Hz, 3H).

Example 3

Scheme 5. Preparation of Compound 003

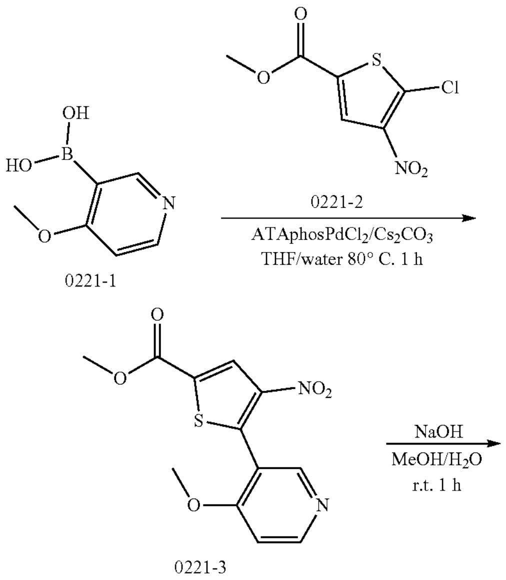

-continued

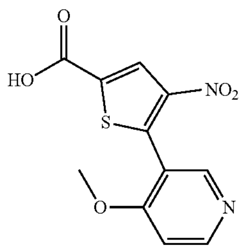

HATU/DIEA
0216-8
DMF r.t. 3 h 0221-4

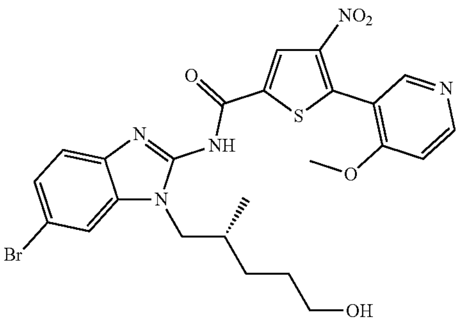

TMSCl/
NaI
ACN/
DMF
50° C.

0221-5

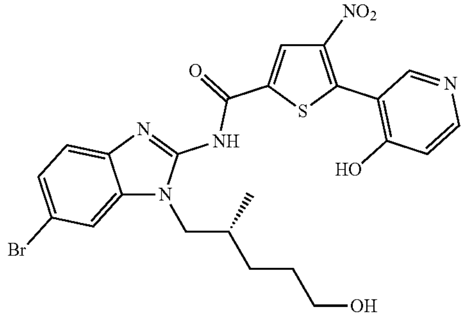

PPh3/
DIAD
THF
r.t.
1 h 0221-6

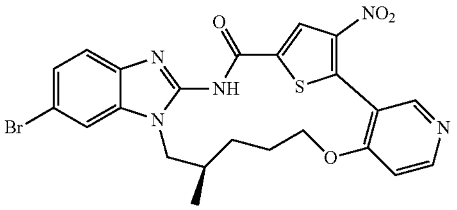

$SnCl_2 \cdot H_2O$
EtOH/NMP
70° C. 3 h 0221-7

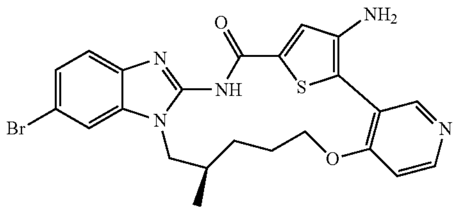

acryloyl
chloride
$NaHCO_3$/
THF 0221-8

-continued

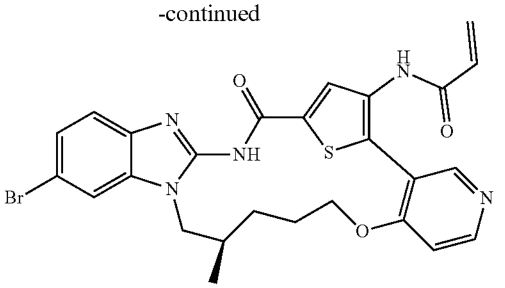

003

Step 1

To a solution of compound 0221-1 (1.9 g, 10.0 mmol) and compound 0221-2 (2.2 g, 10.0 mmol) in THF (40 mL)/water (40 mL) at r.t. were added $ATAphosPdCl_2$ (0.7 g, 1.0 mmol) and $Cs_2CO_3$ (11.4 g, 35.0 mmol). The reaction was heated to 80° C. for 3 h. The reaction was cooled to r.t. and extracted with EtOAc (20 mL×2). The combined organic phases were dried over $Na_2SO_4$ and concentrated under reduce pressure. The crude product was purified through SGC to afford compound 0221-3 (1.7 g, yield 58%) as brown oil. ESI-MS ($EI^+$, m/z): 295. $^1H$ NMR (400 MHz, DMSO-$d_6$) δ 8.62 (d, J=5.9 Hz, 1H), 8.54 (s, 1H), 8.27 (s, 1H), 7.26 (d, J=5.9 Hz, 1H), 3.90 (s, 3H), 3.83 (s, 3H).

Step 2

To a solution of compound 0221-3 (1.7 g, 5.8 mmol) in methanol (20 mL)/water (10 mL) was added NaOH (1N in water, 8.7 mL). The reaction was stirred for 1 h at r.t. The reaction was diluted with water (20 mL) and concentrated under reduce pressure to ⅗ column. The mixture was acidified to pH=3 with 4N HCl. The precipitate was collected by filtration and dried to afford compound 0221-4 (1.2 g, yield 75%) as off-white solid. ESI-MS (Er, m/z): 281. $^1H$ NMR (400 MHz, DMSO-$d_6$) δ 8.61 (d, J=5.8 Hz, 1H), 8.53 (s, 1H), 8.16 (s, 1H), 7.25 (d, J=5.9 Hz, 1H), 3.83 (s, 3H).

Step 3

To a solution of compound 0221-4 (1.1 g, 3.9 mmol) and 0216-8 (1.2 g, 3.9 mmol) in DMF (20 mL) at r.t. was added HATU (2.2 g, 5.9 mmol) and DIEA (1.0 g, 7.8 mmol). The reaction was stirred for 3 h at r.t. The reaction was basified to pH=12 with NaOH (1N) dropwise. The reaction mixture was stirred for 20 min. The reaction mixture was diluted with water (500 mL) and the precipitate was collected by centrifugation. The solid was washed with water (20 mL×2) and dried under reduce pressure. The crude solid was added to methanol (20 mL). The slurry was filtered and the solid was collected to afford compound 0221-5 (1.1 g yield 50%) as light yellow solid. ESI-MS(E1+, m/z): 574. $^1H$ NMR (400 MHz, DMSO-$d_6$) δ 12.86 (s, 1H), 8.60 (d, J=5.8 Hz, 1H), 8.53 (s, 1H), 8.11 (s, 1H), 7.85 (d, J=1.8 Hz, 1H), 7.48 (d, J=8.4 Hz, 1H), 7.41 (dd, J=8.4, 1.7 Hz, 1 H), 7.25 (d, J=5.9 Hz, 1H), 4.35 (t, J=5.1 Hz, 1H), 4.11 (dd, J=13.8, 6.6 Hz, 1H), 4.00 (dd, J=13.8, 8.3 Hz, 1H), 3.84 (s, 3H), 3.37 (d, J=6.0 Hz, 2H), 2.18-2.10 (m, 1H), 1.64-1.51 (m, 1H), 1.48-1.36 (mm, 2H), 1.30-1.17 (m, 1H), 0.86 (d, J=6.7 Hz, 3H).

Step 4

To a solution of compound 0221-5 (1.0 g, 1.7 mmol) in ACN (10 mL)/DMF (10 mL) at r.t. were added TMSCI (1.9 g, 17.4 mmol) and NaI (2.6 g, 17.4 mmol). The reaction was heated to 80° C. for 16 h. The reaction was cooled to r.t. and diluted with water (50 mL). The black precipitate was collected by centrifugation and dissolved in methanol/DCM (30 mL, v/v=⅕). The solvent was dried over $Na_2SO_4$ and concentrated under reduce pressure. The crude product was purified through SGC (methanol/DCM=1/20) to afford compound 0221-6 (400 mg, yield 41%) as yellow solid. ESI-MS(EI$^+$, m/z): 560. $^1$H NMR (400 MHz, DMSO-$d_6$) δ 12.77 (s, 1H), 11.95 (s, 1H), 8.17 (s, 1H), 8.03 (s, 1H), 7.84 (d, J=1.8 Hz, 1H), 7.73 (d, J=7.4 Hz, 1H), 7.47 (d, J=8.5 Hz, 1H), 7.40 (dd, J=8.5, 1.8 Hz, 1H), 6.26 (d, J=7.4 Hz, 1H), 4.37 (t, J=5.0 Hz, 1H), 4.11 (dd, J=13.8, 6.5 Hz, 1H), 4.00 (dd, J=13.8, 8.3 Hz, 1H), 3.41-3.34 (m, 2H), 2.22-2.09 (m, 1H), 1.64-1.53 (m, 1H), 1.52-1.35 (m, 2H), 1.32-1.17 (m, 1H), 0.87 (d, J=6.7 Hz, 3H).

Step 5

To a solution of DIAD (108 mg, 535 umol)/$PPh_3$ (140 mg, 535 umol) in THF (6 mL) at r.t. was added compound 0221-6 (60 mg, 107 umol). The reaction was stirred for 2 h at r.t. The reaction was repeated for 5 times. The combined reaction solvent was poured into water (50 mL), yellow precipitate formed. The precipitate was collected by centrifugation. The solid was dissolved in THF (80 mL), dried over $Na^2SO^4$, and concentrated under reduce pressure. The crude product was purified through SGC (methanol/DCM=1/50) to afford compound 0221-7 (260 mg, yield 78%) as yellow solid. ESI-MS (Er, m/z): 542. $^1$H NMR (400 MHz, 15 DMSO-$d_6$) δ 12.69 (s, 1H), 8.68 (s, 1H), 8.49 (d, J=5.8 Hz, 1H), 7.92 (s, 1H), 7.87 (d, J=1.4 Hz, 1H), 7.38 (d, J=1.5 Hz, 2H), 7.21 (d, J=5.9 Hz, 1H), 4.33 (d, J=9.1 Hz, 1H), 4.14-3.90 (m, 3H), 2.20-2.01 (m, 3H), 1.60-1.40 (m, 2H), 0.87 (d, J=6.5 Hz, 3H).

Step 6

To a solution of compound 0221-7 (80 mg, 147.5 umol) at r.t. in ethanol (1 mL)/NMP (2 mL) was added $SnCl_2 \cdot H_2O$ (153 mg, 137.4 umol). The reaction was heated to 70° C. for 2 h. The reaction was quenched with saturated $NaHCO_3$ (20 mL) aqueous in water, extracted with EtOAc (20 mL×5). The combined organic phase was dried over $Na_2SO_4$ and concentrated under reduce pressure. The crude product was purified through SGC (methanol/DCM=1/10) to afford 0221-8 (40 mg, yield 52.9%) as yellow solid. ESI-MS(EI$^+$, m/z): 512. $^1$H NMR (400 MHz, DMSO-de) δ 12.33 (s, 1H), 8.91 (s, 1H), 8.29 (d, J=5.6 Hz, 1H), 7.76 (d, J=1.2 Hz, 1H), 7.31 (d, J=1.0 Hz, 2H), 7.09 (s, 1H), 7.05 (d, J=5.7 Hz, 1H), 5.24 (s, 2H), 4.29-4.24 (m, 1H), 4.13-4.00 (m, 2H), 3.91-3.83 (m, 1H), 2.37-2.23 (m, 2H), 1.65-1.39 (m, 2H), 0.89 (d, J=6.6 Hz, 3H).

Step 7

To a solution of 0221-8 (10 mg, 19.5 umol) in THF (3 mL)/std aqueous $NaHCO_3$ (0.6 mL) at 0° C. was added dropwise acryloyl chloride (1 M in DCM, 250 uL) over 10 min. The reaction was warmed to r.t. gradually. The reaction was purified by prep-HPLC directly to afford 003 (1.5 mg, yield 13.6%) as yellow solid. $^1$H NMR (400 MHz, DMSO-$d_6$) δ 10.06 (s, 1H), 8.75 (s, 1H), 8.38 (d, J=5.6 Hz, 1H), 7.87-7.56 (m, 3H), 7.26 (dd, J=8.5, 2.0 Hz, 1H), 7.13 (d, J=5.7 Hz, 1H), 6.48 (dd, J=17.1, 10.2 Hz, 1H), 6.25 (dd, J=17.1, 2.1 Hz, 1H), 5.86-5.65 (m, 1H), 4.30 (d, J=9.0 Hz, 2H), 4.14-4.05 (m, 1H), 3.96-3.87 (m, 1H), 2.31-2.24 (m, 2H), 1.64-1.54 (m, 2H), 1.52-1.38 (m, 3H), 0.90 (d, J=6.5 Hz, 3H).

Example 4: HTRF-Based EGFR Biochemical Assays

EGFR biochemical activity measurements were carried out using the homogeneous time-resolved fluorescence (HTRF) assay (Cisbio). Inhibitors and DMSO normalizations were first dispensed to empty black low-volume 384-well plates (Corning) with D300 digital liquid dispenser (HP). All reactions were carried out at room temperature and solutions were added to plates with a Multidrop Combi Reagent Dispenser (ThermoFisher). The reaction mixture (10 μL final volume) contained 1 μM tyrosine kinase peptide-biotin substrate and mutant EGFR in a reaction buffer (50 mM HEPES pH 7.0, 5 mM $MgCl_2$, 1 mM $MnCl_2$, 0.01% BSA, 2 mM TCEP, 0.1 mM $NaVO_4$). Enzyme concentrations were adjusted to accommodate varying kinase activities (L858R$^{0.1}$ nM, L858R/T790M 0.02 nM). Enzyme reaction solution (2× concentrations, 5 μL) was added to 384-well plates containing compounds and incubated for 30 mins. Enzyme reactions were initiated with the addition of 5 μL of ATP to a final concentration of 100 μM and reacted for 20 mins. Reactions were quenched with the addition of 10 μL of phospho-tyrosine antibody-Europium(III) cryptate (1-to-180 volume ratio) and Streptavidin-XL665 (46.7 nM) in EDTA-containing detection buffer, then incubated at room temperature for 1 hour, and read with a PHERAstar plate reader (excitation=337 nm, emission=620 nm and 665 nm). $IC_{50}$ values were determined by inhibition curves (11-point curves from 1.0 μM to 0.130 nM or 23-point curves from 1.0 μM to 0.130 μM) in triplicate with non-linear least squares fit in GraphPad Prism 7.0d. The data obtained are shown in Table 5 below.

TABLE 5

| No. | HTRF $IC_{50}$ EGFR L858R/T790M, nM | HTRF $IC_{50}$ EGFR L858R, nM |
|---|---|---|
| 001 | >100 | >100 |
| 002 | >100 | >100 |

Example 5: Ba/F3 Cell Proliferation Models

The EGFR mutant L858R Ba/F3 cells have been previously described (Zhou, W., et al. *Nature* 462, 2009, 1070-1074). The EGFR $C_{797}S$ and $C_{775}S$ mutations were introduced via site directed mutagenesis using the Quick Change Site-Directed Mutagenesis kit into a vector containing EGFR L858R mutation (Stratagene; La Jolla, CA) according to the manufacturers instructions. All constructs were confirmed by DNA sequencing. The constructs were then shuttled into the retroviral vector JP1540 by either using the Cre-recombination system (Agilent Technologies, Santa Clara, CA) or the In-fusion HD Cloning kit (TakaR$^a$ Bio USA, Inc.; Mountain view, CA). Ba/F3 cells were then infected with retrovirus per standard protocols, as described previously (Zhou, et al, Nature 2009). Stable clones were obtained by selection in puromycin (2 μg/ml). All BaF/3 mutant cells were maintained in RPMI 1640 (Cellgro; Mediatech Inc., Herndon, CA) supplemented with 10% FBS, 100 units/mL penicillin, 100 units/mL streptomycin.

Growth and inhibition of growth was assessed by the Cell Titer Glo assay (Promega, Madison, WI) and was performed according to the manufacturer's instructions. The Cell Titer Glo assay is a luminescence-based method used to determine the number of viable cells based on quantitation of the ATP present, which is directly proportional to the amount of metabolically active cells present. Ba/F3 cells of different EGFR genotypes were exposed to compounds for 72 hours and the number of cells used per experiment was determined empirically as has been previously established (Zhou, et al., Nature 2009). All experimental points were set up in triplicates in 384-well plates. The luminescent signal was detected using a spectrometer and the data was graphically displayed using GraphPad Prism version 5.0 for Windows, (GraphPad Software; www.graphpad.com). The curves were fitted using a non-linear regression model with a sigmoidal dose response. The results of this assay for the compounds disclosed herein are shown in Table 6.

TABLE 6

| No. | Cell $IC_{50}$ BaF3 EGFR L858R, uM | Cell $IC_{50}$ BaF3 EGFR L858R/C797S, uM |
|---|---|---|
| 001 | 2.90 | 1.46 |
| 002 | 4.42 | 3.58 |
| 003 | 4.43 | 4.03 |

Example 6: MS Intact Labeling Assay

EGFR L858R/T790M protein (10 μg) or EGFR L858R/T790M/$C_{797}$S protein was treated with DMSO or a 10-fold molar excess of compound 001 for 2 h at 30° C. and analyzed by LC-MS using an HPLC (Shimadzu, Marlborough, MA) interfaced to an LTQ ion trap mass spectrometer (ThermoFisher Scientific, San Jose, CA). Protein (5 μg) was injected onto a reversed phase column (5 cm POROS 50R2, Applied Biosystems, Foster City, CA), desalted for 4 min (100% A), and gradient eluted (0-100% B in 1 min; A=0.2 M acetic acid in water; B=0.2 M acetic acid in acetonitrile) into the mass spectrometer (spray voltage=4.8 kV). The mass spectrometer was programmed to acquire profile mass spectra (m/z 300-2000). Raw data was deconvoluted using MagTran version 1.03b2.38.

TABLE 7

| Compound 001 | |
|---|---|
| Protein | Percent Labeling |
| L858R/T790M | 80% |
| L858R/T790M/C797S | 80% |

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A compound of Formula I:

(I)

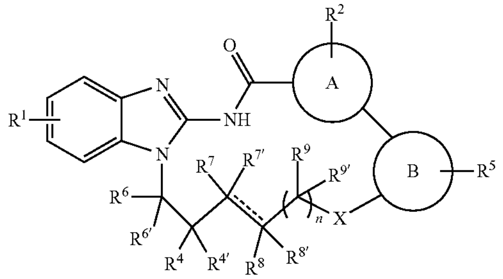

or a pharmaceutically acceptable salt thereof;

wherein:

═ is an optional double bond;

X is O, S, or NH;

A is selected from the group consisting of $C_6$-$C_{10}$ aryl, 5-10 membered heteroaryl, $C_3$-$C_{10}$ cycloalkyl, 3-10 membered heterocycloalkyl, $C_3$-$C_{10}$ cycloalkenyl, and 3-10 membered heterocycloalkenyl;

B is selected from the group consisting of $C_6$-$C_{10}$ aryl, 5-10 membered heteroaryl, $C_3$-$C_{10}$ cycloalkyl, 3-10 membered heterocycloalkyl, $C_3$-$C_{10}$ cycloalkenyl, and 3-10 membered heterocycloalkenyl;

$R^1$ is selected from the group consisting of H, halo, OH, $NH_2$, CN, $NO_2$, $C_{1-6}$ alkyl, NH($C_{1-6}$ alkyl), N($C_{1-6}$ alkyl)$_2$, $C_{1-6}$ haloalkyl, $C_{1-6}$ alkoxy, C(O)-$C_1$-$C_6$ alkyl, C(O)$NH_2$, C(O)NH-$C_1$-$C_6$ alkyl, $C_1$-$C_6$ alkyl-OH, P(O)($C_1$-$C_6$ alkyl)$_2$, $C_6$-$C_{10}$ aryl, 5-10 membered heteroaryl, $C_3$-$C_{10}$ cycloalkyl, and 3-10 membered heterocycloalkyl, wherein $C_{1-6}$ alkyl, $C_6$-$C_{10}$ aryl, 5-10 membered heteroaryl, $C_3$-$C_{10}$ cycloalkyl, and 3-10 membered heterocycloalkyl are each optionally substituted with $R^a$;

$R^4$ is selected from the group consisting of H, halo, OH, $NH_2$, $C_{1-6}$ alkyl, $C_{2-6}$ alkenyl, $C_{2-6}$ alkynyl, NH($C_{1-6}$ alkyl), N($C_{1-6}$ alkyl)$_2$, $C_{1-6}$ haloalkyl, $C_{1-6}$ alkoxy, $C_{1-6}$ alkyl-OH, $C_6$-$C_{10}$ aryl, 5-10 membered heteroaryl, $C_3$-$C_{10}$ cycloalkyl, and 3-10 membered heterocycloalkyl;

$R^5$ is selected from the group consisting of H, halo, OH, $NH_2$, $C_{1-6}$ alkyl, $C_{2-6}$ alkenyl, $C_{2-6}$ alkynyl, NH($C_{1-6}$ alkyl), N($C_{1-6}$ alkyl)$_2$, $C_{1-6}$ haloalkyl, $C_{1-6}$ alkoxy, $C_6$-$C_{10}$ aryl, 5-10 membered heteroaryl, C3-C10 cycloalkyl, and 3-10 membered heterocycloalkyl;

each $R^{4'}$, $R^6$, $R^{6'}$, $R^7$, $R^{7'}$, $R^8$, $R^{8'}$, $R^9$, and $R^{9'}$ is independently selected from the group consisting of H, halo, OH, $NH_2$, $C_{1-6}$ alkyl, $C_{2-6}$ alkenyl, $C_{2-6}$ alkynyl, NH($C_{1-6}$ alkyl), N($C_{1-6}$ alkyl)$_2$, $C_{1-6}$ haloalkyl, $C_{1-6}$ alkoxy, $C_{1-6}$ alkyl-OH, $C_6$-$C_{10}$ aryl, 5-10 membered heteroaryl, $C_3$-$C_{10}$ cycloalkyl, and 3-10 membered heterocycloalkyl; wherein aryl, heteroaryl, cycloalkyl, and heterocycloalkyl are each optionally substituted with C1-3 alkyl;

$R^a$ is selected from the group consisting of $C_6$-$C_{10}$ aryl, 5-10 membered heteroaryl, $C_3$-$C_{10}$ cycloalkyl, and 3-10 membered heterocycloalkyl all of which are optionally substituted with $C_{1-3}$ alkyl;

$R^2$ is selected from the group consisting of:

(i-1)

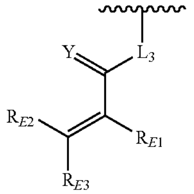

(i-2)

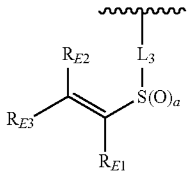

(i-3)

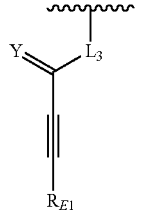

(i-14)

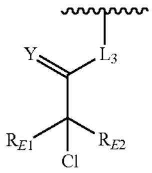

(i-13)

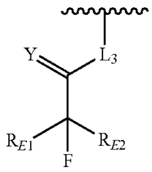

(i-19)

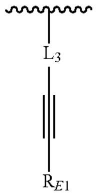

and (i-43)

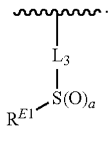

$L_3$ is a bond, -NH-, or $C_1$-$C_4$ alkylene, optionally wherein one or more carbon is independently replaced with —C(O)—, —O—, —S—, —$NR_{L3a}$—, —$NR_{L3a}$C(O)—, —C(O)$NR_{L3a}$—, —SC(O)—, —C(O)S—, —OC(O)—, —C(O)O—, —$NR_{L3a}$C(S)—, —C(S)$NR_{L3a}$—, trans—$CR_{L3b}$═$CR_{L3b}$—, cis—$CR_{L3b}$═$CR_{L3b}$—, —C≡C—, —S(O)—, —S(O)O—, —OS(O)—, —S(O)$NR_{L3a}$—, —$NR_{L3a}$S(O)—, —$S(O)_2$, —$S(O)_2$O—, —$OS(O)_2$—, —$S(O)_2NR_{L3a}$—, or —$NR_{L3a}S(O)_2$—;

$R_{L3a}$ is hydrogen, $C_1$-$C_6$ alkyl optionally substituted with $R^9$, or a nitrogen protecting group;

$R_{L3b}$ is independently, at each occurrence, selected from the group consisting of hydrogen, halogen, $C_1$-$C_6$ alkyl, $C_2C_6$ alkenyl, $C_2$-$C_6$ alkynyl, 3-8 membered cycloalkyl, 3-12 membered heterocycloalkyl, 6-10 membered ary;, and 5-8 membered heteroaryl, wherein alkyl, alkenyl, alkynyl, cycloalkyl, heterocyclyl, aryl, and heteroaryl are optionally substituted with one, two, or three $R^9$;

or, alternatively, two $R_{L3b}$ groups, together with the atoms to which they are attached, from a 3-8membered cycloalkyl or 4-7 membered heterocycloalkyl, both of which are optionally substituted with one, two, or three $R^9$;

each of $R_{E1}$, $R_{E2}$, and $R_{E3}$ is independently selected from the group consisting of hydrogen, halogen, $C_1$-$C_6$ alkyl, $C_2$-$C_6$ alkenyl, $C_2$-$C_6$ alkynyl, 3-12 membered cycloalkyl, 3-12 membered heterocycloalkyl, 6-12 membered aryl, and 5-12 membered heteroaryl, CN, $CH_2OR_{EE}$, $CH_2N(R_{EE})_2$, $CH_2SR_{EE}$, $OR_{EE}$, $N(R_{EE})_2$, $SR_{EE}$, wherein alkyl, alkenyl, alkynyl, cycloalkyl, heterocyclyl, aryl, and heteroaryl are optionally substituted with one, two, or three $R^9$;

or, alternatively, $R_{E1}$ and $R_{E3}$, or $R_{E2}$ and $R_{E3}$, or $R_{E1}$ ad $R_{E2}$ are joined to form 3-8 membered cycloalkyl or 4-7 membered heterocycloalkyl, both of which are optionally substituted with one, two, or three $R^9$;

each $R_{EE}$ is independently selected from the group consisting of hydrogen, $C_1$-$C_6$ alkyl $C_1$-$C_6$ alkoxy, $C_2$-$C_6$ alkenyl, $C_2$-$C_6$ alkynyl, 3-8 membered cycloalkyl, 3-8 membered heterocycloalkyl, 6-10 membered aryl, and 5-10 membered heteroaryl, wherein alkyl, alkenyl, alkynyl, cycloalkyl, heterocyclyl, aryl, and heteroaryl are optionally substituted with one, two, or three $R^9$;

or, alternatively, two $R_{EE}$ groups, together with the atom to which they are attached, form 4-7 membered heterocycloalkyl;

each Y is independently O, S, $CH_2$, or $NR_{E7}$;

$R_{E7}$ is hydrogen or $C_1$-$C_6$ alkyl;

each $R^9$ is independently selected from the group consisting of halo, OH, $NH_2$; NH($C_1$-$C_6$ alkyl), and N($C_1$-$C_6$ alkyl)$_2$;

a is 0, 1, or 2;

n is 0, 1, or 2.

2. The compound of claim 1, wherein the compound of Formula I is a compound of Formula II:

(II)

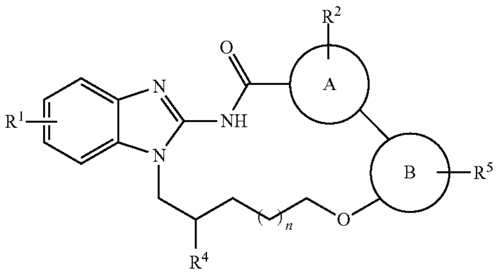

or a pharmaceutically acceptable salt thereof.

3. The compound of claim 1, wherein

A is phenyl or 5-10 membered heteroaryl;

B is phenyl or 5-10 membered heteroaryl;

$R^1$ is selected from the group consisting of H, halo, and $C_{1-6}$ alkyl, wherein alkyl is optionally substituted with $R^a$;

$R^4$ is $C_{1-6}$ alkyl;

$R^5$ is H or $C_{1-6}$ alkyl;

$R^a$ is 5-6 membered heterocycloalkyl substituted with $C_{1-3}$ alkyl;

$R^2$ is (i-1)

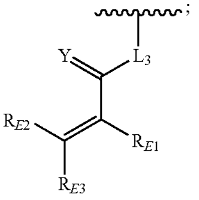

wherein $L_3$ is a bond or —NH—;

each of $R_{E1}$, $R_{E2}$, and $R_{E3}$ is independently selected from the group consisting of hydrogen, halogen, and $C_1$-$C_6$ alkyl;

Y is O or $CH_2$; and n is 0, 1, or 2.

4. The compound of claim 1, wherein A is selected from the group consisting of phenyl, 5-6 membered heteroaryl, $C_3$-$C_8$ cycloalkyl, and 3-8 membered heterocycloalkyl; and B is selected from the group consisting of phenyl, 5-6 membered heteroaryl, $C_3$-$C_8$ cycloalkyl, and 3-8 membered heterocycloalkyl.

5. The compound of claim 1, wherein

A is phenyl or thiophenyl; and

B is selected from the group consisting of phenyl, pyridinyl, pyrazolyl, pyridazinyl, and pyrimidinyl.

6. The compound of claim 1, wherein $R^1$ is selected from the group consisting of H, halo, $C_{1-6}$ alkyl, $NH(C_{1-6}$ alkyl), $N(C_{1-6}$ alkyl$)_2$, $C_{1-6}$ haloalkyl, and $C_{1-6}$ alkoxy, wherein $C_{1-6}$ alkyl is substituted with $R^a$; and $R^a$ is 4-8 membered heterocycloalkyl substituted with methyl.

7. The compound of claim 1, wherein $R^1$ is H, halo, or $C_{1-6}$ alkyl substituted with $R^a$; and $R^a$ is piperazinyl substituted with methyl.

8. The compound of claim 1, wherein each $R^6$, $R^{6'}$, $R^7$, $R^{7'}$, $R^8$, $R^{8'}$, $R^9$, and $R^{9'}$ is H.

9. The compound of claim 1, wherein $R^4$ is H or $C_{1-6}$ alkyl.

10. The compound of claim 1, wherein $R^5$ is H or $C_{1-6}$ alkyl.

11. The compound of claim 1, wherein $R^2$ is selected from the group consisting of

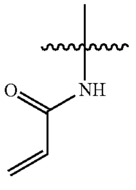
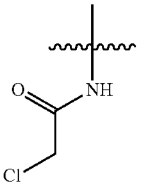
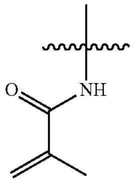
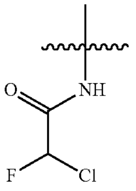

-continued

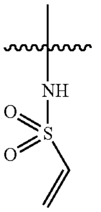
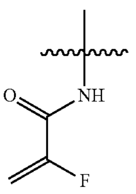
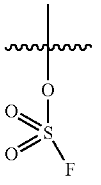
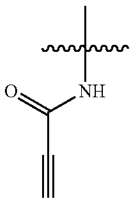
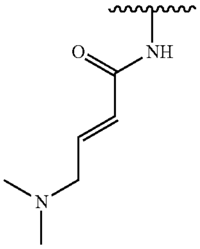
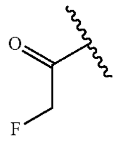
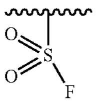

and

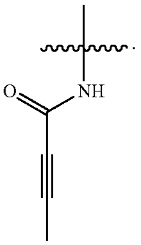

12. The compound of claim 1, wherein the compound of Formula I is selected from the group consisting of

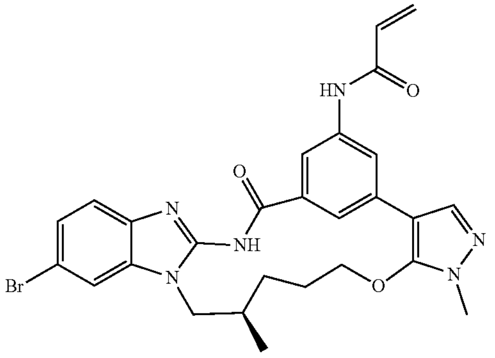

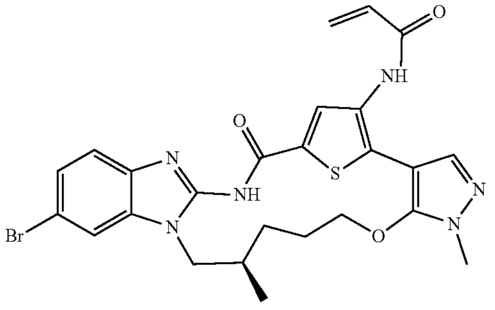

-continued
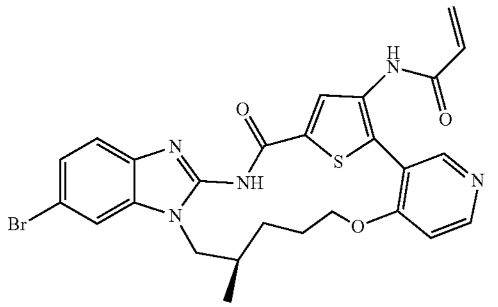
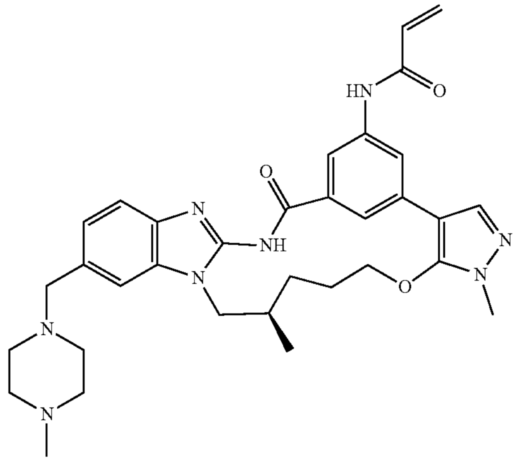
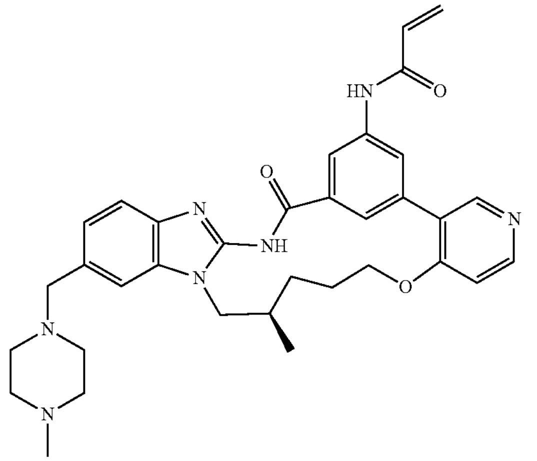
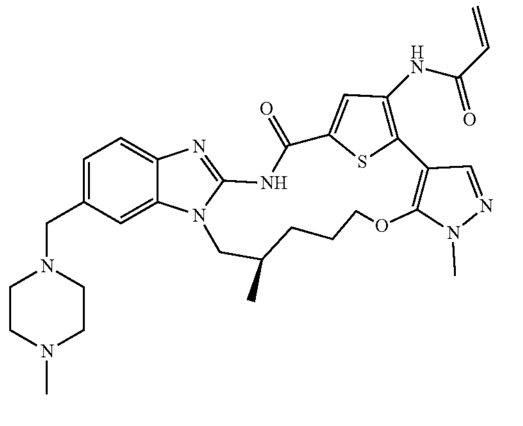
-continued
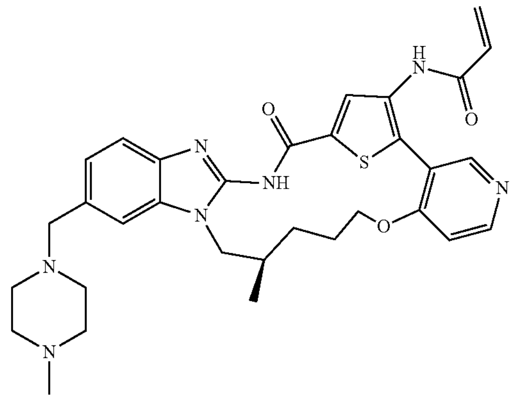
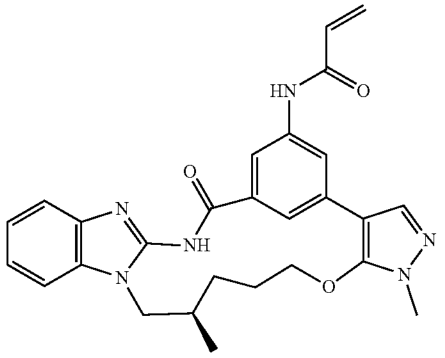
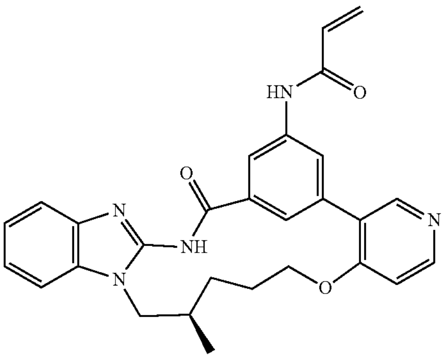
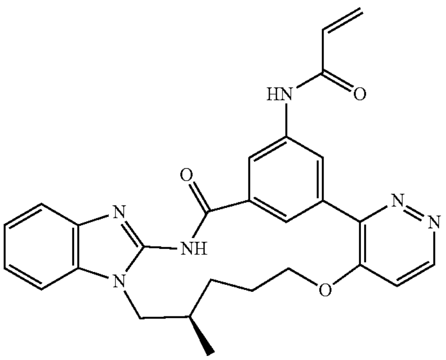

-continued

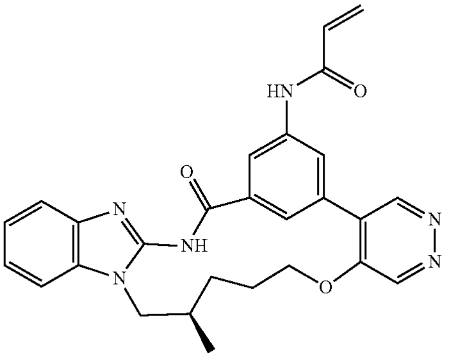

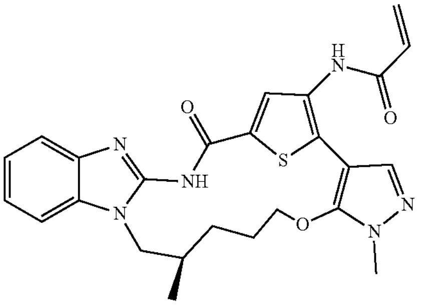

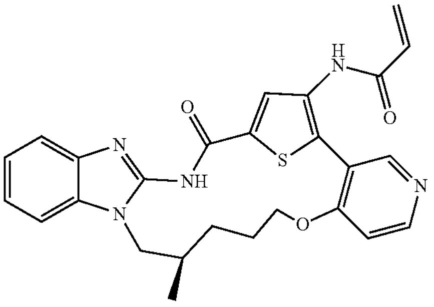

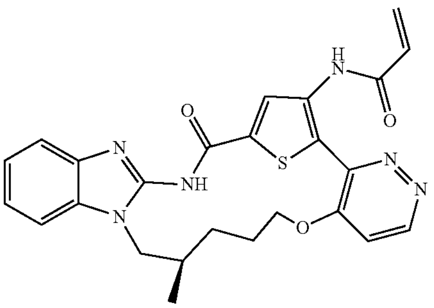

-continued

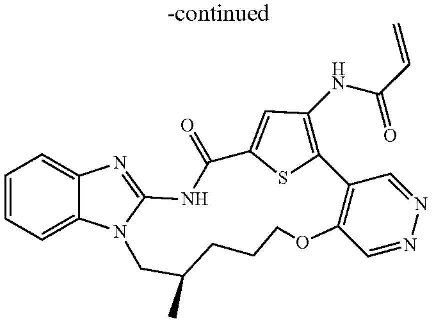

or a pharmaceutically acceptable salt thereof.

13. The compound of claim 1, wherein

X is O;

A is 5-6 membered heteroaryl;

B is 5-6 membered heteroaryl;

$R^1$ is H or halo;

$R^4$ is $C_{1-3}$ alkyl;

$R^5$ is H or $C_{1-3}$ alkyl; and $R^2$ is

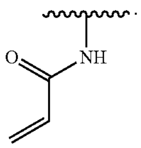

14. The compound of claim 1, wherein

X is O;

A is 5-6 membered heteroaryl;

B is 5-6 membered heteroaryl;

$R^1$ is halo or $C_{1-3}$ alkyl substituted with $R^a$;

$R^4$ is $C_{1-3}$ alkyl;

$R^5$ is H or $C_{1-3}$ alkyl;

$R^a$ is 3-7 membered heterocycloalkyl substituted with methyl; and $R^2$is

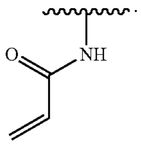 [SMILES: *NC(=O)C=C]

15. A pharmaceutical composition comprising a compound of claim 1, or a pharmaceutically acceptable salt thereof, and a pharmaceutically acceptable carrier.

16. A method of inhibiting the activity of EGFR in a subject in need thereof comprising administering to the subject a therapeutically effective amount of a compound of claim 1.

17. A method of treating cancer in a subject in need thereof comprising administering to the subject a therapeutically effective amount of a compound of claim 1.

18. The method of claim 17, wherein the cancer is selected from the group consisting of lung cancer, colon cancer, breast cancer, endometrial cancer, thyroid cancer, glioma, squamous cell carcinoma, and prostate cancer.

19. The method according to claim 17, wherein the cancer is non-small cell lung cancer (NSCLC).

* * * * *